United States Patent
Sudol et al.

(10) Patent No.: US 11,557,375 B2
(45) Date of Patent: Jan. 17, 2023

(54) METHODS AND SYSTEMS FOR IMPROVED MAJOR HISTOCOMPATIBILITY COMPLEX (MHC)-PEPTIDE BINDING PREDICTION OF NEOEPITOPES USING A RECURRENT NEURAL NETWORK ENCODER AND ATTENTION WEIGHTING

(71) Applicant: NantOmics, LLC, Culver City, CA (US)

(72) Inventors: Jeremi Sudol, New York, NY (US); Kamil Wnuk, Playa del Rey, CA (US)

(73) Assignee: NantOmics, LLC, Culver City, CA (US)

( * ) Notice: Subject to any disclaimer, the term of this patent is extended or adjusted under 35 U.S.C. 154(b) by 0 days.

(21) Appl. No.: 17/059,157

(22) PCT Filed: Aug. 14, 2019

(86) PCT No.: PCT/US2019/046582
§ 371 (c)(1),
(2) Date: Nov. 25, 2020

(87) PCT Pub. No.: WO2020/046587
PCT Pub. Date: Mar. 5, 2020

(65) Prior Publication Data
US 2021/0202043 A1 Jul. 1, 2021

Related U.S. Application Data

(60) Provisional application No. 62/758,297, filed on Nov. 9, 2018, provisional application No. 62/720,081, filed on Aug. 20, 2018.

(51) Int. Cl.
| | |
|---|---|
| *G16B 40/00* | (2019.01) |
| *G16B 5/20* | (2019.01) |
| *G06N 3/04* | (2006.01) |
| *G06N 3/08* | (2006.01) |

(52) U.S. Cl.
CPC .......... *G16B 40/00* (2019.02); *G06N 3/0445* (2013.01); *G06N 3/0454* (2013.01); *G06N 3/08* (2013.01); *G16B 5/20* (2019.02)

(58) Field of Classification Search
None
See application file for complete search history.

(56) References Cited

U.S. PATENT DOCUMENTS

| | | |
|---|---|---|
| 2005/0074809 A1 | 4/2005 | Brusic |
| 2013/0330335 A1 | 12/2013 | Bremel |
| 2015/0278441 A1 | 10/2015 | Min et al. |
| 2016/0132631 A1 | 5/2016 | Bremel et al. |

FOREIGN PATENT DOCUMENTS

| | | |
|---|---|---|
| WO | 2017/184590 A1 | 10/2017 |
| WO | 2017184590 A1 | 10/2017 |

OTHER PUBLICATIONS

Bhattacharya et al. (bioRxiv preprint; posted online Jul. 27, 2017; doi:https//doi.org/10.1101/154757—authors at Johns Hopkins University; pp. 1-25.*
Jurtz et al. (Bioinformatics (2017) vol. 33(22):3685-3690).*
Dey et al. (R. Dey and F. M. Salem, "Gate-variants of Gated Recurrent Unit (GRU) neural networks," 2017 IEEE 60th International Midwest Symposium on Circuits and Systems (MWSCAS), 2017, pp. 1597-1600; e-pp. 1-6).*
International Search Report issued in International Application No. PCT/US2019/046582 dated May 7, 2020, 3 pages.
International Preliminary Report on Patentability issued in International Application No. PCT/US2019/046582 dated Mar. 4, 2021, 6 pages.

* cited by examiner

*Primary Examiner* — Lori A. Clow
(74) *Attorney, Agent, or Firm* — Mauriel Kapouytian Woods LLP; Andrew A. Noble

(57) ABSTRACT

Techniques are provided for predicting MHC-peptide binding affinity. A plurality of training peptide sequences is obtained, and a neural network model is trained to predict MHC-peptide binding affinity using the training peptide sequences. An encoder of the neural network model comprising an RNN is configured to process an input training peptide sequence to generate a fixed-dimension encoding output by applying a final hidden state of the RNN at intermediate state outputs of the RNN to generate attention weighted outputs, and linearly combining the attention weighted outputs. A fully connected layer following the encoder is configured to process the fixed-dimension encoding output to generate an MHC-peptide binding affinity prediction output. A computing device is configured to use the trained neural network to predict MHC-peptide binding affinity for a test peptide sequence.

27 Claims, 16 Drawing Sheets

Specification includes a Sequence Listing.

| A | L | A | T | F | T | V | N | I |
|---|---|---|---|---|---|---|---|---|
| 1 | 0 | 1 | 0 | 0 | 0 | 0 | 0 | 0 |
| 0 | 1 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| • | • | • | • | • | • | • | • | • |
| • | • | • | • | • | • | • | • | • |
| • | • | • | • | • | • | • | • | • |
| 0 | 0 | 0 | 1 | 0 | 1 | 0 | 0 | 0 |
| 0 | 0 | 0 | 0 | 0 | 0 | 1 | 0 | 0 |
| 0 | 0 | 0 | 0 | 0 | 0 | 0 | 0 | 0 |
| 0 | 0 | 0 | 0 | 0 | 0 | 0 | 0 | 0 |

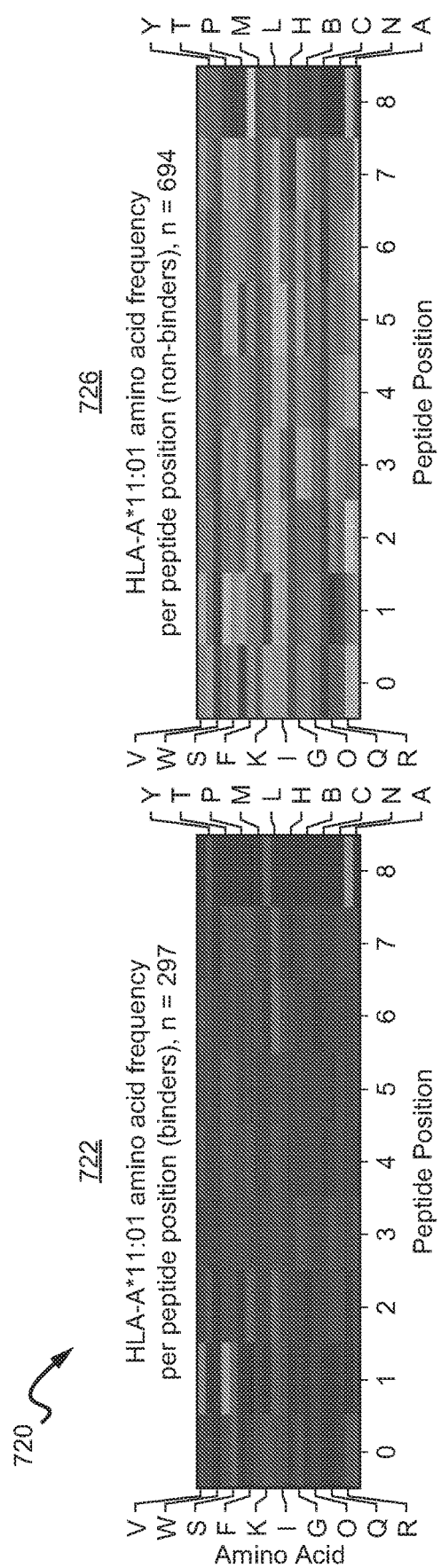
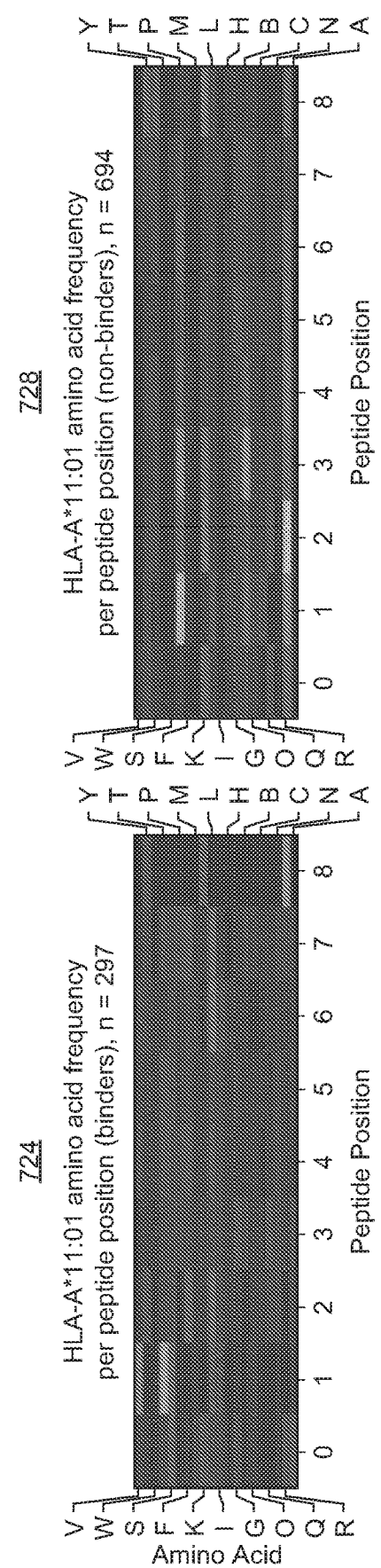
FIG. 7B

| A | B | C | D | E | F | G | H | I | J |
|---|---|---|---|---|---|---|---|---|---|
| | | | | CNN - no padding | | CNN - centered peptide, outer padding (len=13) | | | |
| allele | length | num train examples | num val examples | ROC AUC | PR AUC | ROC AUC combo | ROC AUC combo breakdown | PR AUC combo | PR AUC combo breakdown |
| HLA-A-0101 | 9 | 2725 | 1177 | 0.951 | 0.812 | 0.933 | 0.953 | 0.735 | 0.810 |
| HLA-A-0101 | 10 | 497 | 204 | 0.766 | 0.514 | | 0.811 | | 0.522 |
| HLA-A-0201 | 9 | 6331 | 2719 | 0.943 | 0.893 | 0.937 | 0.946 | 0.878 | 0.900 |
| HLA-A-0201 | 10 | 1931 | 822 | 0.886 | 0.799 | | 0.905 | | 0.819 |
| HLA-A-0202 | 9 | 1734 | 731 | 0.879 | 0.865 | 0.895 | 0.904 | 0.881 | 0.892 |
| HLA-A-0202 | 10 | 1003 | 442 | 0.834 | 0.794 | | 0.877 | | 0.859 |
| HLA-A-0203 | 9 | 3101 | 1326 | 0.931 | 0.898 | 0.926 | 0.941 | 0.895 | 0.911 |
| HLA-A-0203 | 10 | 1128 | 486 | 0.837 | 0.840 | | 0.875 | | 0.867 |
| HLA-A-0206 | 9 | 2607 | 1125 | 0.873 | 0.830 | 0.884 | 0.885 | 0.848 | 0.848 |
| HLA-A-0206 | 10 | 1142 | 481 | 0.860 | 0.834 | | 0.884 | | 0.852 |
| HLA-A-0301 | 9 | 3840 | 1647 | 0.927 | 0.797 | 0.926 | 0.933 | 0.828 | 0.819 |
| HLA-A-0301 | 10 | 1187 | 507 | 0.870 | 0.819 | | 0.892 | | 0.848 |
| HLA-A-1101 | 9 | 3175 | 1368 | 0.940 | 0.869 | 0.925 | 0.939 | 0.854 | 0.866 |
| HLA-A-1101 | 10 | 1181 | 499 | 0.855 | 0.816 | | 0.873 | | 0.832 |
| HLA-A-2402 | 9 | 1368 | 732 | 0.889 | 0.629 | 0.893 | 0.893 | 0.643 | 0.635 |
| HLA-A-2402 | 10 | 496 | 193 | 0.891 | 0.701 | | 0.892 | | 0.666 |
| HLA-A-2601 | 9 | 2642 | 1123 | 0.934 | 0.685 | 0.928 | 0.943 | 0.679 | 0.725 |
| HLA-A-2601 | 10 | 436 | 196 | 0.751 | 0.367 | | 0.828 | | 0.497 |
| HLA-A-2902 | 9 | 1473 | 636 | 0.891 | 0.763 | 0.910 | 0.913 | 0.809 | 0.806 |
| HLA-A-2902 | 10 | 369 | 153 | 0.778 | 0.679 | | 0.888 | | 0.824 |
| HLA-A-3001 | 9 | 1798 | 767 | 0.895 | 0.786 | 0.907 | 0.917 | 0.802 | 0.837 |
| HLA-A-3001 | 10 | 199 | 89 | 0.759 | 0.394 | | 0.801 | | 0.368 |
| HLA-A-3101 | 9 | 2764 | 1180 | 0.924 | 0.778 | 0.908 | 0.928 | 0.775 | 0.796 |
| HLA-A-3101 | 10 | 1145 | 495 | 0.810 | 0.679 | | 0.856 | | 0.739 |
| HLA-A-6801 | 9 | 1415 | 620 | 0.907 | 0.862 | 0.897 | 0.910 | 0.859 | 0.871 |
| HLA-A-6801 | 10 | 1165 | 486 | 0.860 | 0.839 | | 0.879 | | 0.846 |
| HLA-A-6802 | 9 | 2560 | 1111 | 0.921 | 0.795 | 0.920 | 0.928 | 0.818 | 0.832 |
| HLA-A-6802 | 10 | 1142 | 475 | 0.859 | 0.720 | | 0.901 | | 0.794 |
| HLA-A-6901 | 9 | 1790 | 767 | 0.874 | 0.535 | n/a | n/a | n/a | n/a |
| HLA-A-6901 | 10 | 0 | 0 | n/a | n/a | | n/a | | n/a |
| HLA-B-0702 | 9 | 2702 | 1165 | 0.941 | 0.829 | 0.940 | 0.949 | 0.847 | 0.863 |
| HLA-B-0702 | 10 | 405 | 166 | 0.850 | 0.742 | | 0.871 | | 0.772 |
| HLA-B-0801 | 9 | 2117 | 909 | 0.929 | 0.771 | 0.928 | 0.935 | 0.772 | 0.787 |
| HLA-B-0801 | 10 | 257 | 108 | 0.774 | 0.547 | | 0.860 | | 0.655 |
| HLA-B-1501 | 9 | 2862 | 1238 | 0.909 | 0.783 | 0.924 | 0.921 | 0.824 | 0.803 |
| HLA-B-1501 | 10 | 185 | 67 | 0.852 | 0.929 | | 0.923 | | 0.963 |
| HLA-B-1801 | 9 | 1623 | 692 | 0.821 | 0.349 | 0.878 | 0.881 | 0.510 | 0.502 |
| HLA-B-1801 | 10 | 245 | 108 | 0.719 | 0.457 | | 0.852 | | 0.572 |
| HLA-B-2705 | 9 | 1976 | 834 | 0.946 | 0.709 | 0.941 | 0.951 | 0.743 | 0.743 |
| HLA-B-2705 | 10 | 213 | 104 | 0.887 | 0.773 | | 0.851 | | 0.758 |
| HLA-B-3501 | 9 | 1765 | 748 | 0.917 | 0.829 | 0.898 | 0.922 | 0.782 | 0.835 |
| HLA-B-3501 | 10 | 360 | 163 | 0.745 | 0.525 | | 0.739 | | 0.448 |
| HLA-B-4001 | 9 | 1978 | 845 | 0.969 | 0.826 | 0.960 | 0.978 | 0.796 | 0.872 |
| HLA-B-4001 | 10 | 345 | 150 | 0.782 | 0.604 | | 0.818 | | 0.494 |
| HLA-B-5101 | 9 | 1568 | 671 | 0.920 | 0.539 | 0.910 | 0.932 | 0.573 | 0.633 |
| HLA-B-5101 | 10 | 348 | 150 | 0.685 | 0.354 | | 0.811 | | 0.386 |
| HLA-B-5801 | 9 | 1768 | 760 | 0.955 | 0.850 | 0.946 | 0.959 | 0.791 | 0.838 |
| HLA-B-5801 | 10 | 177 | 76 | 0.730 | 0.402 | | 0.742 | | 0.460 |
| HLA-B-5801 | 9 | 2903 | 891 | 0.948 | 0.837 | 0.948 | 0.961 | 0.845 | 0.877 |
| HLA-B-5801 | 10 | 164 | 76 | 0.784 | 0.629 | | 0.763 | | 0.605 |
| mean | | | | 0.864 | 0.712 | 0.919 | 0.890 | 0.783 | 0.745 |
| mean HLA-A 910 | | | | 0.872 | 0.745 | 0.914 | 0.896 | 0.808 | 0.781 |
| mean HLA-A 9 | | | | 0.912 | 0.786 | | 0.924 | | 0.825 |
| mean HLA-A 10 | | | | 0.830 | 0.700 | | 0.869 | | 0.738 |
| mean HLA-B 910 | | | | 0.853 | 0.664 | 0.927 | 0.881 | 0.748 | 0.693 |
| mean HLA-B 9 | | | | 0.926 | 0.732 | | 0.939 | | 0.775 |
| mean HLA-B 10 | | | | 0.781 | 0.596 | | 0.823 | | 0.611 |
| mean HLA-AB 9 | | | | 0.917 | 0.765 | | 0.930 | | 0.804 |
| mean HLA-AB 10 | | | | 0.809 | 0.657 | | 0.850 | | 0.685 |

| 1008 (CNN - marginalize over paddings (len=13)) | | | | 1010 (RNN (onehot, bidir, GRU, ADAM lr=0.00008, fc drop = 0.1)) | | | | | |
|---|---|---|---|---|---|---|---|---|---|
| K | L | M | N | O | P | Q | R | S | T |
| ROC AUC combo | ROC AUC combo breakdown | PR AUC combo | PR AUC combo breakdown | ROC AUC single-length | ROC AUC combo | ROC AUC combo breakdown | PR AUC single-length | PR AUC combo | PR AUC combo breakdown |
| 0.933 | 0.943 / 0.865 | 0.771 | 0.794 / 0.682 | 0.959 / 0.820 | 0.946 | 0.960 / 0.859 | 0.848 / 0.614 | 0.812 | 0.841 / 0.699 |
| 0.932 | 0.940 / 0.907 | 0.874 | 0.891 / 0.829 | 0.951 / 0.900 | 0.941 | 0.949 / 0.908 | 0.909 / 0.823 | 0.887 | 0.905 / 0.831 |
| 0.867 | 0.874 / 0.857 | 0.837 | 0.842 / 0.831 | 0.901 / 0.877 | 0.905 | 0.907 / 0.901 | 0.884 / 0.860 | 0.888 | 0.890 / 0.885 |
| 0.924 | 0.933 / 0.895 | 0.896 | 0.892 / 0.905 | 0.948 / 0.886 | 0.935 | 0.947 / 0.898 | 0.914 / 0.885 | 0.913 | 0.915 / 0.911 |
| 0.874 | 0.871 / 0.882 | 0.833 | 0.824 / 0.855 | 0.879 / 0.868 | 0.888 | 0.885 / 0.896 | 0.846 / 0.832 | 0.858 | 0.851 / 0.874 |
| 0.920 | 0.920 / 0.905 | 0.811 | 0.784 / 0.851 | 0.943 / 0.897 | 0.933 | 0.937 / 0.911 | 0.833 / 0.845 | 0.834 | 0.819 / 0.864 |
| 0.926 | 0.937 / 0.884 | 0.861 | 0.866 / 0.856 | 0.950 / 0.886 | 0.938 | 0.947 / 0.905 | 0.886 / 0.858 | 0.884 | 0.884 / 0.887 |
| 0.887 | 0.884 / 0.897 | 0.657 | 0.638 / 0.714 | 0.907 / 0.904 | 0.911 | 0.905 / 0.925 | 0.652 / 0.710 | 0.689 | 0.658 / 0.796 |
| 0.916 | 0.918 / 0.908 | 0.688 | 0.676 / 0.728 | 0.940 / 0.899 | 0.931 | 0.936 / 0.894 | 0.740 / 0.676 | 0.750 | 0.763 / 0.700 |
| 0.904 | 0.900 / 0.906 | 0.801 | 0.787 / 0.837 | 0.912 / 0.865 | 0.913 | 0.921 / 0.868 | 0.818 / 0.768 | 0.812 | 0.816 / 0.800 |
| 0.911 | 0.915 / 0.850 | 0.804 | 0.827 / 0.469 | 0.926 / 0.727 | 0.916 | 0.924 / 0.804 | 0.857 / 0.440 | 0.830 | 0.852 / 0.407 |
| 0.898 | 0.914 / 0.856 | 0.748 | 0.754 / 0.739 | 0.929 / 0.859 | 0.915 | 0.931 / 0.871 | 0.810 / 0.752 | 0.789 | 0.804 / 0.760 |
| 0.889 | 0.902 / 0.871 | 0.851 | 0.866 / 0.836 | 0.921 / 0.901 | 0.919 | 0.936 / 0.896 | 0.886 / 0.878 | 0.895 | 0.908 / 0.881 |
| 0.903 | 0.902 / 0.902 | 0.789 | 0.793 / 0.793 | 0.935 / 0.916 | 0.930 | 0.932 / 0.926 | 0.839 / 0.823 | 0.836 | 0.831 / 0.845 |
| n/a | n/a / n/a | n/a | n/a / n/a | 0.928 / n/a | n/a | n/a / n/a | 0.631 / n/a | n/a | n/a / n/a |
| 0.927 | 0.935 / 0.877 | 0.811 | 0.826 / 0.771 | 0.955 / 0.847 | 0.944 | 0.951 / 0.891 | 0.879 / 0.710 | 0.857 | 0.865 / 0.818 |
| 0.908 | 0.918 / 0.828 | 0.761 | 0.780 / 0.626 | 0.938 / 0.746 | 0.920 | 0.931 / 0.812 | 0.819 / 0.476 | 0.773 | 0.791 / 0.618 |
| 0.903 | 0.899 / 0.916 | 0.779 | 0.752 / 0.940 | 0.931 / 0.947 | 0.933 | 0.929 / 0.957 | 0.816 / 0.969 | 0.840 | 0.816 / 0.975 |
| 0.822 | 0.816 / 0.847 | 0.407 | 0.368 / 0.609 | 0.913 / 0.898 | 0.896 | 0.909 / 0.857 | 0.535 / 0.519 | 0.542 | 0.553 / 0.641 |
| 0.945 | 0.942 / 0.935 | 0.738 | 0.683 / 0.859 | 0.957 / 0.925 | 0.956 | 0.953 / 0.965 | 0.767 / 0.878 | 0.803 | 0.762 / 0.946 |
| 0.884 | 0.903 / 0.788 | 0.745 | 0.818 / 0.470 | 0.920 / 0.818 | 0.907 | 0.927 / 0.797 | 0.839 / 0.658 | 0.798 | 0.840 / 0.596 |
| 0.951 | 0.969 / 0.825 | 0.779 | 0.866 / 0.542 | 0.980 / 0.833 | 0.961 | 0.980 / 0.826 | 0.902 / 0.643 | 0.790 | 0.898 / 0.541 |
| 0.908 | 0.916 / 0.862 | 0.600 | 0.625 / 0.502 | 0.916 / 0.863 | 0.928 | 0.936 / 0.889 | 0.604 / 0.561 | 0.630 | 0.650 / 0.564 |
| 0.937 | 0.947 / 0.798 | 0.758 | 0.793 / 0.547 | 0.972 / 0.839 | 0.959 | 0.969 / 0.795 | 0.877 / 0.619 | 0.839 | 0.882 / 0.485 |
| 0.928 | 0.940 / 0.729 | 0.795 | 0.828 / 0.560 | 0.967 / 0.845 | 0.955 | 0.969 / 0.746 | 0.891 / 0.694 | 0.876 | 0.902 / 0.615 |
| 0.908 | 0.890 | 0.766 | 0.748 | 0.901 | 0.928 | 0.906 | 0.771 | 0.809 | 0.784 |
| 0.906 | 0.898 / 0.911 / 0.885 | 0.801 | 0.791 / 0.802 / 0.780 | 0.901 / 0.929 / 0.872 | 0.923 | 0.910 / 0.930 / 0.890 | 0.797 / 0.823 / 0.769 | 0.834 | 0.817 / 0.838 / 0.796 |
| 0.911 | 0.880 / 0.919 / 0.841 / 0.914 / 0.866 | 0.717 | 0.688 / 0.734 / 0.643 / 0.774 / 0.723 | 0.900 / 0.945 / 0.856 / 0.935 / 0.865 | 0.936 | 0.899 / 0.945 / 0.853 / 0.936 / 0.875 | 0.733 / 0.793 / 0.673 / 0.811 / 0.729 | 0.775 | 0.738 / 0.796 / 0.680 / 0.821 / 0.747 |

*FIG. 10B*

Example Client-Server Relationship

1100

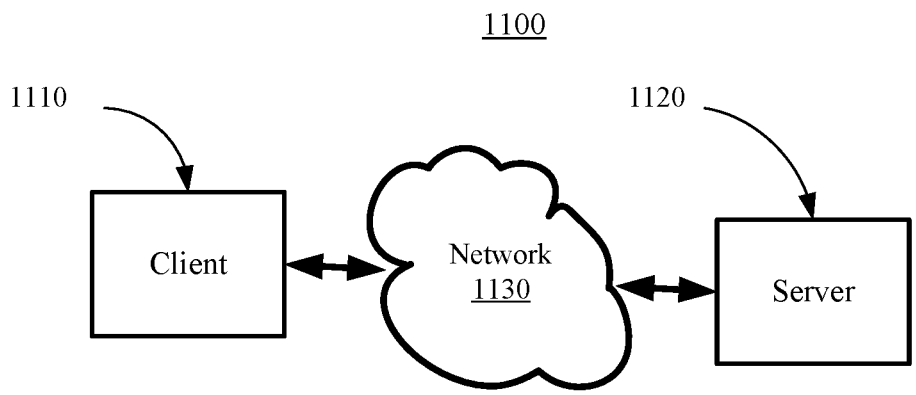

- Obtain test peptide sequence
- Access trained neural network model
- Input test peptide sequence into trained neural network model
- Generate MHC-peptide binding affinity prediction

- Obtain plurality of training peptide sequences
- Configure encoder comprising a recurrent neural network (RNN) to process input training peptide sequence to generate fixed-dimension encoding output by applying final hidden state of the RNN at intermediate state outputs of RNN to generate attention weighted outputs, and linearly combining attention weighted outputs
- Configure fully connected layer to process fixed-dimension encoding output to generate MHC-peptide binding affinity prediction output
- Train neural network model using the plurality of training peptide sequences
- Configure computing device to use trained neural network model to generate MHC-peptide binding affinity prediction for test peptide sequence

FIG. 11

SEQUENCE LISTING

```
<160> NUMBER OF SEQ ID NOS: 53

<210> SEQ ID NO 1
<211> LENGTH: 9
<212> TYPE: PRT
<213> ORGANISM: Homo sapiens

<400> SEQUENCE: 1

Ala Leu Ala Thr Phe Thr Val Asn Ile
1               5

<210> SEQ ID NO 2
<211> LENGTH: 9
<212> TYPE: PRT
<213> ORGANISM: Homo sapiens
```

-continued

```
<400> SEQUENCE: 2

Val Trp Ser Phe Lys Ile Gly Gln Arg
1               5

<210> SEQ ID NO 3
<211> LENGTH: 10
<212> TYPE: PRT
<213> ORGANISM: Homo sapiens

<400> SEQUENCE: 3

Tyr Thr Pro Met Leu His Asx Cys Asn Ala
1               5                   10

<210> SEQ ID NO 4
<211> LENGTH: 9
<212> TYPE: PRT
<213> ORGANISM: Homo sapiens

<400> SEQUENCE: 4

Thr Gln Ile Gln Thr Arg Arg Ser Phe
1               5

<210> SEQ ID NO 5
<211> LENGTH: 10
<212> TYPE: PRT
<213> ORGANISM: Homo sapiens

<400> SEQUENCE: 5

Leu Thr Tyr Ser Gln Leu Met Thr Leu Lys
1               5                   10

<210> SEQ ID NO 6
<211> LENGTH: 9
<212> TYPE: PRT
<213> ORGANISM: Homo sapiens

<400> SEQUENCE: 6

Ser Trp Glu Tyr Trp Gly Ala Gln Leu
1               5

<210> SEQ ID NO 7
<211> LENGTH: 10
<212> TYPE: PRT
<213> ORGANISM: Homo sapiens

<400> SEQUENCE: 7

Met Val Thr Phe Lys Val Pro His Ala Lys
1               5                   10

<210> SEQ ID NO 8
<211> LENGTH: 9
<212> TYPE: PRT
<213> ORGANISM: Homo sapiens

<400> SEQUENCE: 8

Ala Glu His Asp Pro Trp Trp Ala Val
1               5

<210> SEQ ID NO 9
<211> LENGTH: 9
<212> TYPE: PRT
<213> ORGANISM: Homo sapiens

<400> SEQUENCE: 9
```

Lys Ile Arg Leu Arg Pro Gly Gly Lys
1               5

<210> SEQ ID NO 10
<211> LENGTH: 10
<212> TYPE: PRT
<213> ORGANISM: Homo sapiens

<400> SEQUENCE: 10

Ser Met Lys Leu Asn Val Ser Leu Ala His
1               5                   10

<210> SEQ ID NO 11
<211> LENGTH: 9
<212> TYPE: PRT
<213> ORGANISM: Homo sapiens

<400> SEQUENCE: 11

Ala Ile Ile Thr Pro Ile Val Phe Tyr
1               5

<210> SEQ ID NO 12
<211> LENGTH: 10
<212> TYPE: PRT
<213> ORGANISM: Homo sapiens

<400> SEQUENCE: 12

Val Met Cys Gly Gly Ser Leu Tyr Val Lys
1               5                   10

<210> SEQ ID NO 13
<211> LENGTH: 10
<212> TYPE: PRT
<213> ORGANISM: Homo sapiens

<400> SEQUENCE: 13

Val Val Arg Asp Phe Glu Asn Tyr Val Lys
1               5                   10

<210> SEQ ID NO 14
<211> LENGTH: 9
<212> TYPE: PRT
<213> ORGANISM: Homo sapiens

<400> SEQUENCE: 14

Glu Pro Ala Asp His Leu Ala Ile Met
1               5

<210> SEQ ID NO 15
<211> LENGTH: 11
<212> TYPE: PRT
<213> ORGANISM: Homo sapiens

<400> SEQUENCE: 15

Arg Val Glu Gln Ala Val Glu Ser Met Val Lys
1               5                   10

<210> SEQ ID NO 16
<211> LENGTH: 9
<212> TYPE: PRT
<213> ORGANISM: Homo sapiens

<400> SEQUENCE: 16

Glu Met Ala Asp Tyr Ile Phe Phe Val
1               5

<210> SEQ ID NO 17
<211> LENGTH: 9
<212> TYPE: PRT
<213> ORGANISM: Homo sapiens

<400> SEQUENCE: 17

Gly Ser Glu Asp Arg Asp Leu Leu Tyr
1               5

<210> SEQ ID NO 18
<211> LENGTH: 9
<212> TYPE: PRT
<213> ORGANISM: Homo sapiens

<400> SEQUENCE: 18

Asp Thr Phe Gly Val Ile Asp Thr Met
1               5

<210> SEQ ID NO 19
<211> LENGTH: 9
<212> TYPE: PRT
<213> ORGANISM: Homo sapiens

<400> SEQUENCE: 19

Thr Thr Tyr Met Asp Thr Phe Phe Arg
1               5

<210> SEQ ID NO 20
<211> LENGTH: 9
<212> TYPE: PRT
<213> ORGANISM: Homo sapiens

<400> SEQUENCE: 20

Arg Leu Lys Phe Ser Leu Ser Tyr Lys
1               5

<210> SEQ ID NO 21
<211> LENGTH: 9
<212> TYPE: PRT
<213> ORGANISM: Homo sapiens

<400> SEQUENCE: 21

Tyr Arg Ser Gly Ile Ile Ala Val Val
1               5

<210> SEQ ID NO 22
<211> LENGTH: 9
<212> TYPE: PRT
<213> ORGANISM: Homo sapiens

<400> SEQUENCE: 22

Gly Val Tyr Ser Val Phe Tyr Leu Tyr
1               5

<210> SEQ ID NO 23
<211> LENGTH: 9
<212> TYPE: PRT
<213> ORGANISM: Homo sapiens

<400> SEQUENCE: 23

Phe Pro Ala Ser His Met Ala Thr Tyr
1               5

<210> SEQ ID NO 24
<211> LENGTH: 10
<212> TYPE: PRT
<213> ORGANISM: Homo sapiens

<400> SEQUENCE: 24

Ile Ile Lys Ser Asp His Glu Phe Val Lys
1               5                   10

<210> SEQ ID NO 25
<211> LENGTH: 10
<212> TYPE: PRT
<213> ORGANISM: Homo sapiens

<400> SEQUENCE: 25

Phe Leu Pro Ser Asp Phe Phe Pro Ser Val
1               5                   10

<210> SEQ ID NO 26
<211> LENGTH: 9
<212> TYPE: PRT
<213> ORGANISM: Homo sapiens

<400> SEQUENCE: 26

Tyr Met Phe Glu Ser Lys Ser Met Lys
1               5

<210> SEQ ID NO 27
<211> LENGTH: 9
<212> TYPE: PRT
<213> ORGANISM: Homo sapiens

<400> SEQUENCE: 27

Thr Val Leu Pro Leu Glu Phe Ala Arg
1               5

<210> SEQ ID NO 28
<211> LENGTH: 9
<212> TYPE: PRT
<213> ORGANISM: Homo sapiens

<400> SEQUENCE: 28

Glu Arg Tyr Leu Lys Asp Gln Gln Leu
1               5

<210> SEQ ID NO 29
<211> LENGTH: 9
<212> TYPE: PRT
<213> ORGANISM: Homo sapiens

<400> SEQUENCE: 29

Lys Ala Phe Gly Leu Tyr Lys Ser Ile
1               5

<210> SEQ ID NO 30
<211> LENGTH: 9
<212> TYPE: PRT
<213> ORGANISM: Homo sapiens

<400> SEQUENCE: 30

Asn Ala Met Val Thr Leu Arg Lys Glu
1               5

<210> SEQ ID NO 31
<211> LENGTH: 9

```
<212> TYPE: PRT
<213> ORGANISM: Homo sapiens

<400> SEQUENCE: 31

Leu Thr Ile Lys Asp Ser Ser Asn Lys
1               5

<210> SEQ ID NO 32
<211> LENGTH: 9
<212> TYPE: PRT
<213> ORGANISM: Homo sapiens

<400> SEQUENCE: 32

Ala Asn Cys Ser Ser Ile Ser Ile Lys
1               5

<210> SEQ ID NO 33
<211> LENGTH: 9
<212> TYPE: PRT
<213> ORGANISM: Homo sapiens

<400> SEQUENCE: 33

Thr His Glu Ala Asn Thr Met Ala Met
1               5

<210> SEQ ID NO 34
<211> LENGTH: 9
<212> TYPE: PRT
<213> ORGANISM: Homo sapiens

<400> SEQUENCE: 34

Val Gly Tyr Val Asp Asp Thr Gln Phe
1               5

<210> SEQ ID NO 35
<211> LENGTH: 10
<212> TYPE: PRT
<213> ORGANISM: Homo sapiens

<400> SEQUENCE: 35

Arg Gln Val Val Asn Val Ile Thr Thr Lys
1               5                   10

<210> SEQ ID NO 36
<211> LENGTH: 9
<212> TYPE: PRT
<213> ORGANISM: Homo sapiens

<400> SEQUENCE: 36

Leu Ser Phe Ala Ser Leu Phe Leu Pro
1               5

<210> SEQ ID NO 37
<211> LENGTH: 9
<212> TYPE: PRT
<213> ORGANISM: Homo sapiens

<400> SEQUENCE: 37

Leu Gln Leu Thr Ala Val Phe Ala Tyr
1               5

<210> SEQ ID NO 38
<211> LENGTH: 9
<212> TYPE: PRT
<213> ORGANISM: Homo sapiens
```

<400> SEQUENCE: 38

Asp Val Ser Pro Leu Met His Leu Phe
1               5

<210> SEQ ID NO 39
<211> LENGTH: 11
<212> TYPE: PRT
<213> ORGANISM: Homo sapiens

<400> SEQUENCE: 39

Ala Tyr Ile Ser Ser Glu Ala Thr Thr Pro Val
1               5                   10

<210> SEQ ID NO 40
<211> LENGTH: 9
<212> TYPE: PRT
<213> ORGANISM: Homo sapiens

<400> SEQUENCE: 40

Arg Arg Trp Ile Ala Pro His Pro Leu
1               5

<210> SEQ ID NO 41
<211> LENGTH: 9
<212> TYPE: PRT
<213> ORGANISM: Homo sapiens

<400> SEQUENCE: 41

His Thr Tyr His Leu Glu Asn Asp Lys
1               5

<210> SEQ ID NO 42
<211> LENGTH: 10
<212> TYPE: PRT
<213> ORGANISM: Homo sapiens

<400> SEQUENCE: 42

Thr Leu Val Pro Gln Glu His Tyr Val Arg
1               5                   10

<210> SEQ ID NO 43
<211> LENGTH: 9
<212> TYPE: PRT
<213> ORGANISM: Homo sapiens

<400> SEQUENCE: 43

Ile Val Thr Ala Phe Ser Val Ile Lys
1               5

<210> SEQ ID NO 44
<211> LENGTH: 9
<212> TYPE: PRT
<213> ORGANISM: Homo sapiens

<400> SEQUENCE: 44

Cys His Ala Thr Leu Thr His Arg Leu
1               5

<210> SEQ ID NO 45
<211> LENGTH: 9
<212> TYPE: PRT
<213> ORGANISM: Homo sapiens

<400> SEQUENCE: 45

Val Arg Gly Gly Met Val Ala Pro Leu
1               5

<210> SEQ ID NO 46
<211> LENGTH: 9
<212> TYPE: PRT
<213> ORGANISM: Homo sapiens

<400> SEQUENCE: 46

Tyr Ser Asp Ile Phe Asn Asn Val Leu
1               5

<210> SEQ ID NO 47
<211> LENGTH: 9
<212> TYPE: PRT
<213> ORGANISM: Homo sapiens

<400> SEQUENCE: 47

Ala Val Arg Glu Ala Thr Ala Ala Phe
1               5

<210> SEQ ID NO 48
<211> LENGTH: 10
<212> TYPE: PRT
<213> ORGANISM: Homo sapiens

<400> SEQUENCE: 48

Thr Leu Trp Lys Ala Gly Ile Leu Tyr Lys
1               5                   10

<210> SEQ ID NO 49
<211> LENGTH: 10
<212> TYPE: PRT
<213> ORGANISM: Homo sapiens

<400> SEQUENCE: 49

Ser Ile Leu Ser Pro Phe Leu Pro Leu Leu
1               5                   10

<210> SEQ ID NO 50
<211> LENGTH: 9
<212> TYPE: PRT
<213> ORGANISM: Homo sapiens

<400> SEQUENCE: 50

Phe Leu Arg Ser Ile Ala Met Leu Lys
1               5

<210> SEQ ID NO 51
<211> LENGTH: 9
<212> TYPE: PRT
<213> ORGANISM: Homo sapiens

<400> SEQUENCE: 51

Glu Ser Lys Ala Lys Gln Leu Cys Tyr
1               5

<210> SEQ ID NO 52
<211> LENGTH: 9
<212> TYPE: PRT
<213> ORGANISM: Homo sapiens

<400> SEQUENCE: 52

Lys Leu Tyr Lys Met Arg Ile Pro Arg

```
<210> SEQ ID NO 53
<211> LENGTH: 9
<212> TYPE: PRT
<213> ORGANISM: Homo sapiens

<400> SEQUENCE: 53

Met Ile Ser Arg Met Leu Ile Asn Arg
1               5
```

METHODS AND SYSTEMS FOR IMPROVED MAJOR HISTOCOMPATIBILITY COMPLEX (MHC)-PEPTIDE BINDING PREDICTION OF NEOEPITOPES USING A RECURRENT NEURAL NETWORK ENCODER AND ATTENTION WEIGHTING

CROSS REFERENCE TO RELATED APPLICATIONS

This application is a U.S. national phase application of International Application No. PCT/US2019/046582 filed on Aug. 14, 2019, which claims priority to U.S. Provisional Application No. 62/720,081 filed Aug. 20, 2018, and U.S. Provisional Application No. 62/758,297 filed Nov. 9, 2018. The entire contents of these applications are hereby incorporated herein by reference.

TECHNICAL FIELD

This disclosure relates generally to predicting major histocompatibility complex (MHC)-peptide binding, and more specifically to neural network models that employ one or more recurrent neural networks for generating MHC-peptide binding affinity predictions.

REFERENCE TO SEQUENCE LISTING

This application contains a Sequence Listing in electronic format. The Sequence Listing file, titled Sequence_Listing_Protein_Sequence_ST25_1.txt, was created on Oct. 12, 2021, and is 8,528 bytes in size. The information in electronic format of the Sequence Listing is incorporated herein by reference in its entirety.

BACKGROUND

T-cells, or T-lymphocytes, are a type of lymphocyte (a subtype of white blood cell) that plays a central role in cell-mediated immunity. A unique feature of T-cells is their ability to discriminate between healthy and abnormal (e.g. infected or cancerous) cells in the body. Healthy cells typically express a large number of self-derived peptide-major histocompatibility complexes (pMHC) on their cell surface and, although the T-cell antigen receptor can interact with at least a subset of these self-derived pMHC, the T-cell generally ignores these healthy cells. However, when the same cells contain even minute quantities of pathogen-derived pMHC, T-cells can become activated and initiate immune responses. Positively selected T-cells will have an affinity with pMHC and serve useful functions in the body, including the interaction with MHC and peptide complexes to effect immune responses, while negatively selected T-cells that bind too strongly to self-antigens expressed on MHC molecules are obliterated to allow for tolerance of self by the immune system.

Cytotoxic T-cells (a.k.a. TC cells, CTLs, T-killer cells, killer T-cells), destroy virus-infected cells and tumor cells. These cells, also known as CD8 T-cells since they express the CD8 glycoprotein at their surfaces, recognize virus-infected or tumor cell targets by binding to fragments of non-self proteins (peptide antigens) that are generally between 8-15 amino acids in length and presented by major histocompatibility complex (MHC) class I molecules. Peptides of a specific length are often called 'N-mers' for short. For example, peptide sequences that are 9 amino acids in length may be referred to as 9-mers.

MHC class I molecules are one of two primary classes of major histocompatibility complex (MHC) molecules (the other being MHC class II) and are present on the surface of all nucleated cells in humans. Their function is to display intracellular peptide antigens to cytotoxic T-cells, thereby triggering an immediate response from the immune system against the particular non-self antigen displayed.

A current challenge in immunology is understanding what kinds of peptides bind well with what kinds of MHC class I molecules, i.e., which peptides are best for activating a cytotoxic T-cell response, particularly since each allele (variant form) of an MHC compound has different properties. If such MHC-peptide binding affinities could be accurately predicted for protein fragments of various lengths, new immunotherapies could be developed, e.g., based on determining which tumor antigens would be most likely to trigger an immune system response.

Neural networks have been employed to predict MHC-peptide binding affinity. While MHC Class I molecules can bind peptides 6-20 amino acids in length (though generally they are 8-15 amino acids in length) and MHC Class II molecules can bind peptides 10-30 amino acids in length (though generally they are 12-25 amino acids in length), one current drawback is that the inputs to these neural network models are generally fixed in length and do not accommodate variable peptide sequence lengths without padding (i.e., adding one or more '0' or null values to encoded peptide sequences to match the fixed input length of the neural network). While such padding has been shown to have no predictive performance impact when neural networks are trained using single-length peptide sequences (e.g., datasets containing only 9-mer peptide sequences, only 10-mer peptide sequences, etc.), current neural network models using such padding are unable to reach their full predictive performance potential when trained with variable length peptide sequences. As such, there remains a need for techniques that improve MHC-peptide binding affinity prediction performance when neural networks are trained using variable length peptide sequences. Further, it would improve MHC-peptide binding affinity prediction performance to be able to determine the peptide positions of a test input sequence that are most important for predicting MHC-peptide binding affinity.

SUMMARY

Apparatuses, systems, methods, and articles of manufacture related to using a neural network model to predict MHC-peptide binding affinity are described herein. The various embodiments are based on a neural network model that employs a recurrent neural network encoder and attention weighting for generating MHC-peptide binding affinity predictions with improved accuracy when trained with variable length peptide sequences. As such, accurate MHC-peptide binding affinity predictions can be made for test peptide sequences that are similar to training peptide sequences for which binding affinity data is known, but different in length.

In one embodiment, a plurality of training peptide sequences is obtained, and a neural network model is configured to be trained to predict MHC-peptide binding affinity using the training peptide sequences. An encoder of the neural network model comprising a recurrent neural network (RNN) is configured to process an input training peptide sequence to generate a fixed-dimension encoding output by applying a final hidden state of the RNN at intermediate state outputs of the RNN to generate attention weighted outputs, and linearly combining the attention weighted outputs. Each of the attention weighted outputs may be a single value and correspond to an amino acid position of the input training peptide sequence. The neural network model is trained using the plurality of batches of training peptide sequences, and a computing device is configured to use the trained neural network model to predict MHC-peptide binding affinity for a test peptide sequence.

In some embodiments, the RNN may comprise a Long Short Term Memory (LSTM) RNN or a Gated Recurrent Unit (GRU) RNN, or any variants thereof.

In some embodiments, the RNN may comprise a bidirectional RNN, and the fixed-dimension encoding output may be determined by concatenating outputs of the bidirectional RNN.

In some embodiments, applying the final hidden state at an intermediate state output of the RNN to generate an attention weighted output may comprise taking a dot product of the final hidden state and the intermediate state output.

In some embodiments, weights learned through the training of the neural network model may be applied to the final hidden state prior to applying the final hidden state at intermediate state outputs of the RNN to generate attention weighted outputs.

In some embodiments, the final hidden state may be concatenated with a final hidden state of an encoder of a second neural network model prior to applying the final hidden state at intermediate state outputs of the RNN to generate attention weighted outputs. The second neural network model may be configured to predict MHC-peptide binding affinity for an MHC allele input.

In some embodiments, the training peptide sequences may comprise a plurality of sequence lengths between 6-20 or 10-30 amino acids in length, and may be one of one-hot, BLOSUM, PAM, or learned embedding encoded. Each training peptide sequence may be a positive MHC-peptide binding example.

In some embodiments, the test peptide sequence may have a sequence length between 6-20 or 10-30 amino acids in length. The test peptide sequence may have a sequence length different from a sequence length of at least one of the training peptide sequences and may be one of one-hot, BLOSUM, PAM, or learned embedding encoded.

In some embodiments, each MHC-peptide binding prediction output may be a single prediction, and the MHC-peptide binding affinity prediction for the test peptide sequence may be associated with activating a T-cell response to a tumor.

In some embodiments, at least one fully connected layer (e.g., two fully connected layers) following the encoder may be configured to process the fixed-dimension encoding output to generate an MHC-peptide binding affinity prediction output. The at least one fully connected layer may comprise one of a deep convolutional neural network, a residual neural network, a densely connected convolutional neural network, a fully convolutional neural network, or an RNN.

In some embodiments, predicting MHC-peptide binding affinity for the test peptide sequence may comprise processing the test training peptide sequence using the encoder of the trained neural network model to generate a fixed-dimension encoding output by applying a final hidden state of the RNN at intermediate state outputs of the RNN to generate attention weighted outputs, and linearly combining the attention weighted outputs, and processing the fixed-dimension encoding output using the at least one fully connected layer of the trained neural network model to generate an MHC-peptide binding affinity prediction output.

Various objects, features, aspects and advantages of the inventive subject matter will become more apparent from the following specification, along with the accompanying drawings in which like numerals represent like components.

BRIEF DESCRIPTION OF THE DRAWINGS

FIG. 7B illustrates a visualization of attention weights determined for peptide positions of input peptide sequences (SEQ. NOS. 2-3) in accordance with an embodiment.

FIG. 10 illustrates a graphical representation of neural network validation performance for variable-length peptide sequences using a neural network model in accordance with an embodiment versus alternative approaches.

FIG. 11 illustrates a block diagram of an exemplary client-server relationship that can be used for implementing one or more aspects of the various embodiments.

Figure 1:
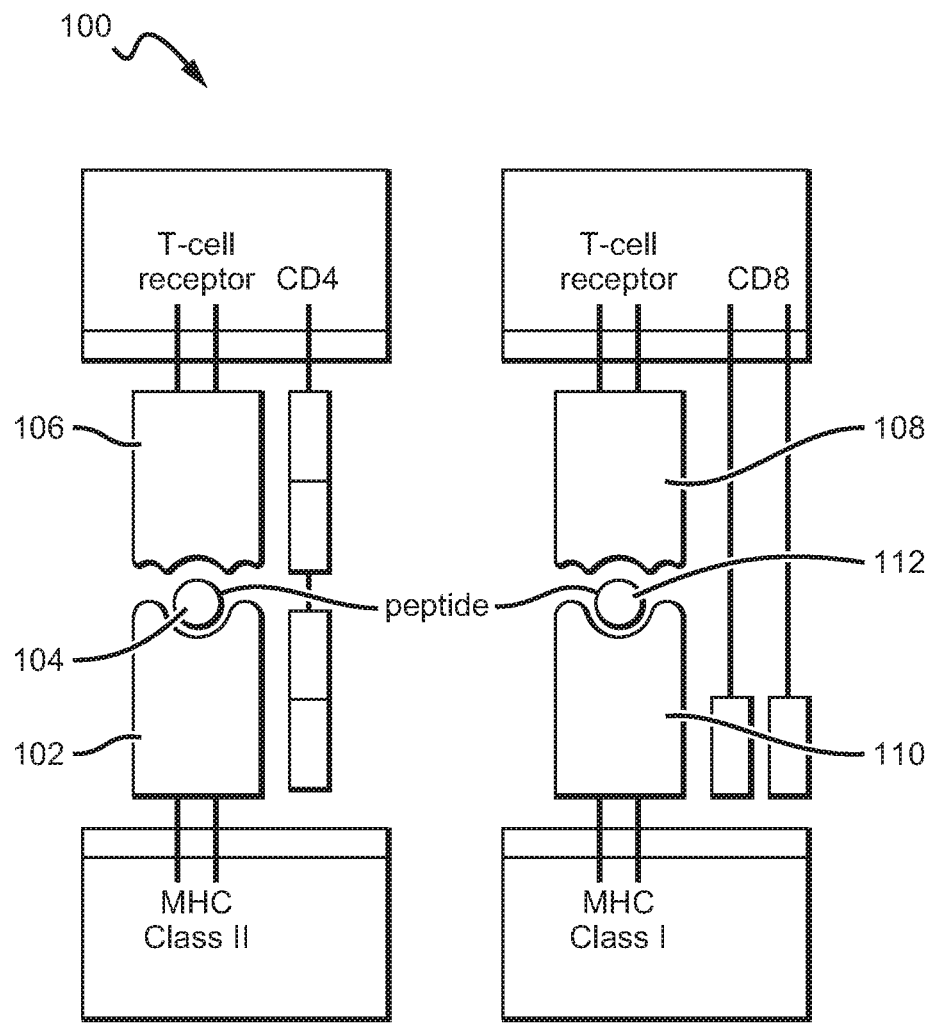
FIG. 1 illustrates a visual representation of MHC molecules binding with peptides at a surface of a nucleated cell in accordance with an embodiment.

While the invention is described with reference to the above drawings, the drawings are intended to be illustrative, and other embodiments are consistent with the spirit, and within the scope, of the invention.

SPECIFICATION

The various embodiments now will be described more fully hereinafter with reference to the accompanying drawings, which form a part hereof, and which show, by way of illustration, specific examples of practicing the embodiments. This specification may, however, be embodied in many different forms and should not be construed as being limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

Throughout the specification and claims, the following terms take the meanings explicitly associated herein, unless the context clearly dictates otherwise:

The phrase "in one embodiment" as used herein does not necessarily refer to the same embodiment, though it may. Thus, as described below, various embodiments of the invention may be readily combined, without departing from the scope or spirit of the invention.

As used herein, the term "or" is an inclusive "or" operator and is equivalent to the term "and/or," unless the context clearly dictates otherwise.

The term "based on" is not exclusive and allows for being based on additional factors not described, unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of a networked environment where two or more components or devices are able to exchange data, the terms "coupled to" and "coupled with" are also used to mean "communicatively coupled with", possibly via one or more intermediary devices.

In addition, throughout the specification, the meaning of "a", "an", and "the" includes plural references, and the meaning of "in" includes "in" and "on".

Although some of the various embodiments presented herein constitute a single combination of inventive elements, it should be appreciated that the inventive subject matter is considered to include all possible combinations of the disclosed elements. As such, if one embodiment comprises elements A, B, and C, and another embodiment comprises elements B and D, then the inventive subject matter is also considered to include other remaining combinations of A, B, C, or D, even if not explicitly discussed herein. Further, the transitional term "comprising" means to have as parts or members, or to be those parts or members. As used herein, the transitional term "comprising" is inclusive or open-ended and does not exclude additional, unrecited elements or method steps.

Throughout the following discussion, numerous references will be made regarding servers, services, interfaces, engines, modules, clients, peers, portals, platforms, or other systems formed from computing devices. It should be appreciated that the use of such terms is deemed to represent one or more computing devices having at least one processor (e.g., ASIC, FPGA, DSP, x86, ARM, ColdFire, GPU, multi-core processors, etc.) configured to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or functions. One should further appreciate the disclosed computer-based algorithms, processes, methods, or other types of instruction sets can be embodied as a computer program product comprising a non-transitory, tangible computer readable medium storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, or other electronic information exchanging methods. Data exchanges can be conducted over a packet-switched network, a circuit-switched network, the Internet, LAN, WAN, VPN, or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

The focus of the disclosed inventive subject matter is to enable construction or configuration of a computing device to operate on vast quantities of digital data, beyond the capabilities of a human for purposes including predicting MHC-peptide binding affinity for variable-length peptide sequences.

One should appreciate that the disclosed techniques provide many advantageous technical effects including improving the scope, accuracy, compactness, efficiency and speed of predicting MHC-peptide binding affinity for variable-length peptide sequences using a neural network model. It should also be appreciated that the following specification is not intended as an extensive overview, and as such, concepts may be simplified in the interests of clarity and brevity.

Predicting MHC-Peptide Binding Affinity for Variable Length Peptide Sequences Using a Recurrent Neural Network Encoder and Attention Weighting In current neural network-based MHC-peptide binding affinity prediction models, the neural network inputs are generally fixed length and do not accommodate variable length peptide sequences without padding (i.e., adding one or more '0' or null values to encoded peptide sequences to match the fixed length of the neural network input). While such padding has been shown to have no performance impact on neural networks trained using single-length peptide sequences (e.g., datasets containing only 9-mer peptide sequences, only 10-mer peptide sequences, etc.), each of the current prediction models has shown that room for improved predictive performance remains when trained using variable length peptide sequences combined using a single padding approach.

However, the performance limitations of MHC-peptide binding affinity prediction models can be improved upon by a neural network model comprising a recurrent neural network encoder configured to use attention weighting for peptide positions of an input peptide sequence. Once trained, such a neural network model can determine attention weights for the peptide positions of a test input sequence and generate an MHC-peptide binding affinity prediction with increased accuracy based on the attention weights.

FIG. 1 illustrates a visual representation of MHC molecules binding with peptides at a surface of a nucleated cell in accordance with an embodiment. Representation 100 illustrates an MHC class II molecule 102 that presents a stably bound peptide 104 that is essential for overall immune function. MHC Class II molecule 102 mainly interacts with immune cells, such as helper (CD4) T-cell 106. For example, peptide 104 (e.g., an antigen) may regulate how CD4 T-cell 106 responds to an infection. In general, stable peptide binding is essential to prevent detachment and degradation of a peptide, which could occur without secure attachment to the MHC Class II molecule 102. Such detachment and degradation would prevent T-cell recognition of the antigen, T-cell recruitment, and a proper immune response. CD4 T-cells, so named because they express the CD4 glycoprotein at their surface, are useful in the antigenic activation of CD8 T-cells, such as CD8 T-cell 108. Therefore, the activation of CD4 T-cells can be beneficial to the action of CD8 T-cells.

CD8 T-cell 108 is a cytotoxic T-cell that expresses the CD8 glycoprotein at its surface. Cytotoxic T-cells (also known as TC cells, CTLs, T-killer cells, killer T-cells) destroy virus-infected cells and tumor cells. These cells recognize virus-infected or tumor cell targets by binding to fragments of non-self proteins (peptide antigens) that are between 6-20 amino acids in length (though generally they are 8-15 amino acids in length) and presented by major histocompatibility complex (MHC) class I molecules, such as MHC class I molecule 110. MHC class I molecules are present on the surface of all nucleated cells in humans. Their function is to display intracellular peptide antigens, e.g., peptide 112, to cytotoxic T-cells, thereby triggering an immediate response from the immune system against the peptide antigen displayed. An understanding what kinds of peptides bind well with what kinds of MHC class I molecules (i.e., which peptides are best for activating a cytotoxic T-cell response) is critical for current immunology research, particularly since each allele (variant form) of an MHC compound has different properties. The embodiments herein improve the operation of neural network-based MHC-peptide binding affinity prediction models by generating more accurate predictions using combined variable-length training peptide sequences.

Figure 2:
FIG. 2 illustrates an example of a one-hot encoded peptide sequence (SEQ. NO. 1) in accordance with an embodiment.

FIG. 2 illustrates an example of a one-hot encoded peptide sequence in accordance with an embodiment. In an exemplary embodiment, training peptide sequences may be one-hot encoded sequences of any length for the techniques described herein. For example, one-hot encoded matrix 200 represents a one-hot encoding of a 9-mer protein/peptide sequence "ALATFTVNI" SEQ. NO. 1, where the single letter codes are used to represent the 20 naturally occurring amino acids. In one-hot encoded matrix 200, legal combinations of values are only those with a single high ("1") bit while the other values are low ("0"). While a 9-mer protein/peptide sequence is shown in FIG. 2, the training peptide sequences described herein may comprise a plurality of sequence lengths between 6-20 or 10-30 amino acids in length. Further, as an alternative to the one-hot encoding shown in FIG. 2, training peptide sequences may be encoded for the techniques described herein as a BLOcks Substitution Matrix (BLOSUM) of the type often used for sequence alignment of proteins, a point accepted mutation (PAM) matrix where each column and row represents one of the 20 standard amino acids, or be learned embedding encoded.

Figure 3:
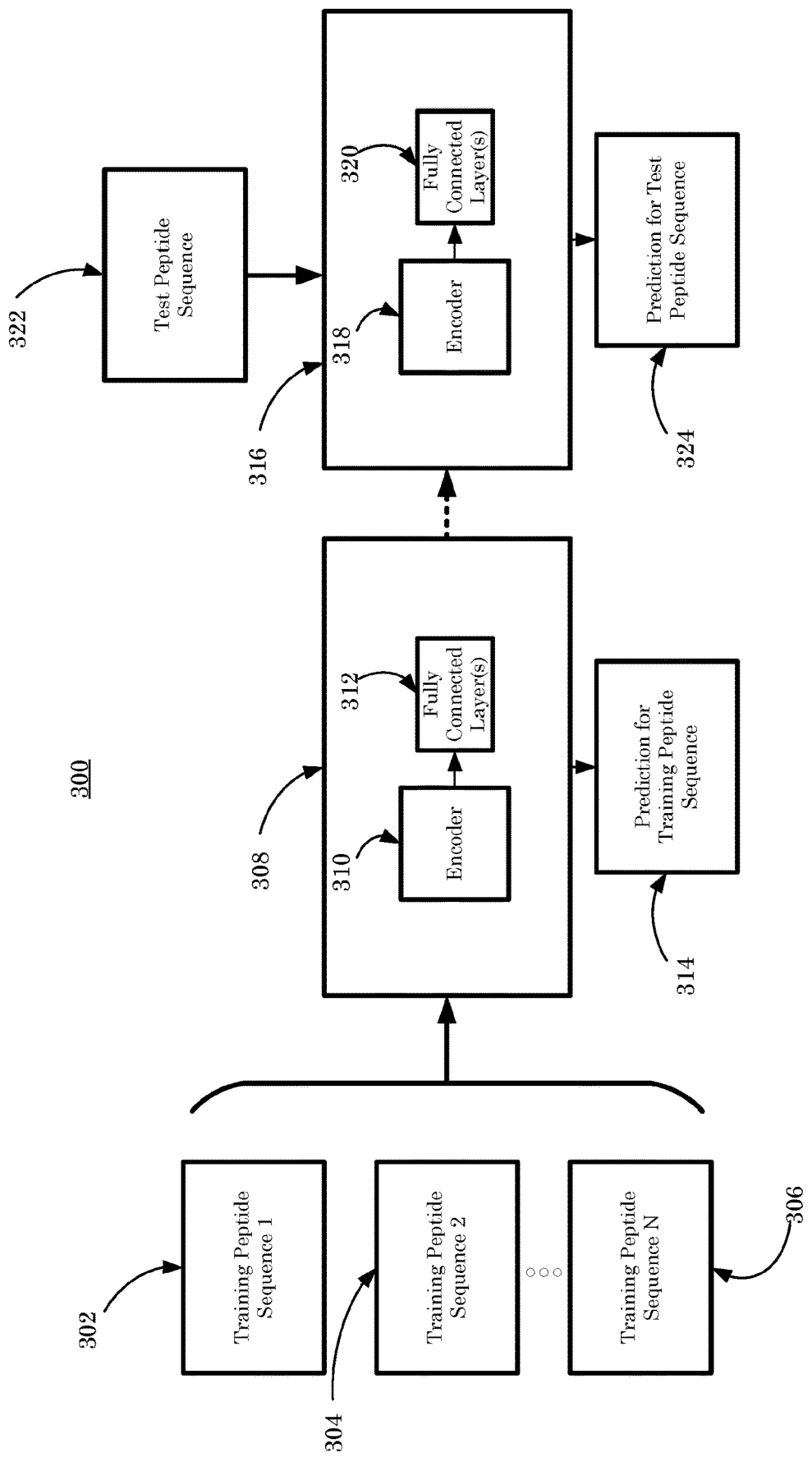
FIG. 3 illustrates an overview flow diagram of example operations for predicting MHC-peptide binding affinity in accordance with an embodiment.

FIG. 3 illustrates an overview flow diagram of example operations for predicting MHC-peptide binding affinity in accordance with an embodiment. In flow diagram 300, variable-length training peptide sequences 1 to N 302, 304, and 306 are used to train neural network model 308 to predict MHC-peptide binding affinity. In accordance with the embodiments herein, neural network model 308 is configured to be trained to predict MHC-peptide binding affinity using a plurality of (e.g., batches of) the training peptide sequences 1 to N 302, 304, and 306. In an embodiment, encoder 310 of neural network model 308 comprises a recurrent neural network (RNN) configured to process an input training peptide sequence to generate a fixed-dimension encoding output by applying a final hidden state of the RNN at intermediate state outputs of the RNN to generate attention weighted outputs, and linearly combining the attention weighted outputs. At least one fully connected layer 312 following encoder 310 may be configured to process the fixed-dimension encoding output to generate an MHC-peptide binding affinity prediction output 314 for the input training peptide sequence. Once the training is completed, the trained neural network 316, comprising trained encoder 318 and at least one trained fully connected layer 320, can be configured to receive a test peptide sequence 322. In accordance with an embodiment, test peptide sequence 322 is likewise processed by trained encoder 318 to generate a fixed-dimension encoding output by applying a final hidden state of the RNN at intermediate state outputs of the RNN to generate attention weighted outputs, and linearly combining the attention weighted outputs. At least one trained fully connected layer 320 following trained encoder 318 may be configured to process the fixed-dimension encoding output to generate an MHC-peptide binding affinity prediction output 324 for input test peptide sequence 322.

Figure 4:
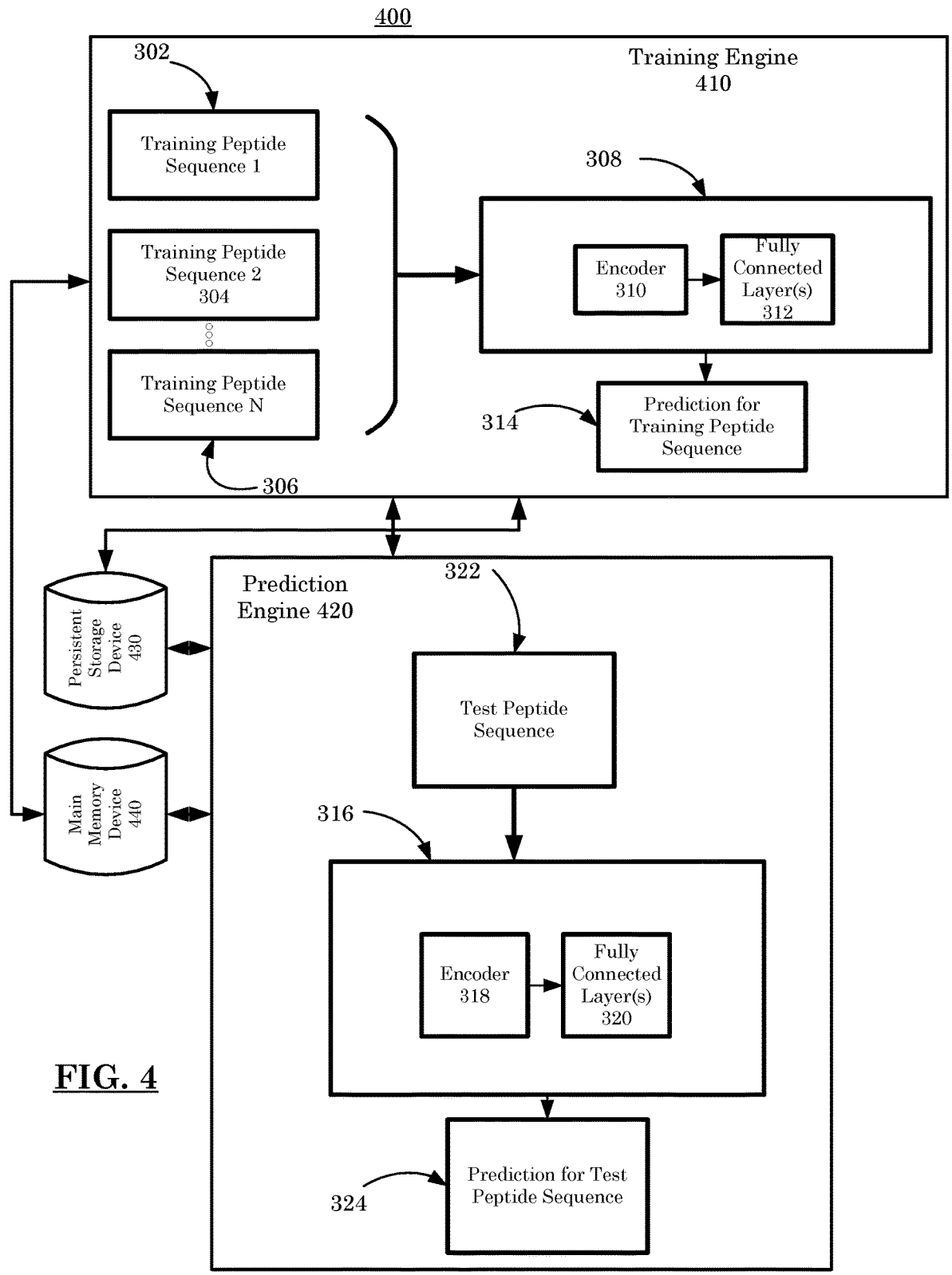
FIG. 4 illustrates a block diagram of a system for predicting MHC-peptide binding affinity in accordance with an embodiment.

FIG. 4 illustrates a block diagram of a system for predicting MHC-peptide binding affinity in accordance with an embodiment. In block diagram 400, elements for predicting MHC-peptide binding affinity in a test peptide sequence include training engine 410, prediction engine 420, persistent storage device 430, and main memory device 440. In an embodiment, training engine 410 may be configured to obtain training peptide sequences 1 to N 302, 304, and 306 from either one or both of persistent storage device 430 and main memory device 440. Training engine 410 may then configure and train neural network model 308, which may be stored in either one or both of persistent storage device 430 and main memory device 440, using the training peptide sequences 1 to N 302, 304, 306 as training inputs. For example, training engine 410 may configure encoder 310 of neural network model 308 comprising a recurrent neural network (RNN) to process an input training peptide sequence to generate a fixed-dimension encoding output by applying a final hidden state of the RNN at intermediate state outputs of the RNN to generate attention weighted outputs, and linearly combining the attention weighted outputs. At least one fully connected layer 312 following encoder 310 may be configured by training engine 410 to process the fixed-dimension encoding output to generate an MHC-peptide binding affinity prediction output 314 for the input training peptide sequence. Training engine 410 also may configure prediction engine 420 to use the trained neural network model 316 to predict MHC-peptide binding affinity in a genomic sample input comprising a test peptide sequence 322. For example, prediction engine 420 may obtain test peptide sequence 322 and predict MHC-peptide binding affinity by processing test peptide sequence 322 via trained encoder 318 to generate a fixed-dimension encoding output by applying a final hidden state of the RNN at intermediate state outputs of the RNN to generate attention weighted outputs, and linearly combining the attention weighted outputs. At least one trained fully connected layer 320 following trained encoder 318 may then process the fixed-dimension encoding output to generate an MHC-peptide binding affinity prediction output 324 for input test peptide sequence 322.

It should be noted that the elements in FIG. 4, and the various functions attributed to each of the elements, while exemplary, are described as such solely for the purposes of ease of understanding. One skilled in the art will appreciate that one or more of the functions ascribed to the various elements may be performed by any one of the other elements, and/or by an element (not shown) configured to perform a combination of the various functions. Therefore, it should be noted that any language directed to a training engine 410, a prediction engine 420, a persistent storage device 430 and a main memory device 440 should be read to include any suitable combination of computing devices, including servers, interfaces, systems, databases, agents, peers, engines, controllers, modules, or other types of computing devices operating individually or collectively to perform the functions ascribed to the various elements. Further, one skilled in the art will appreciate that one or more of the functions of the system of FIG. 4 described herein may be performed within the context of a client-server relationship, such as by one or more servers, one or more client devices (e.g., one or more user devices) and/or by a combination of one or more servers and client devices.

Figure 5:
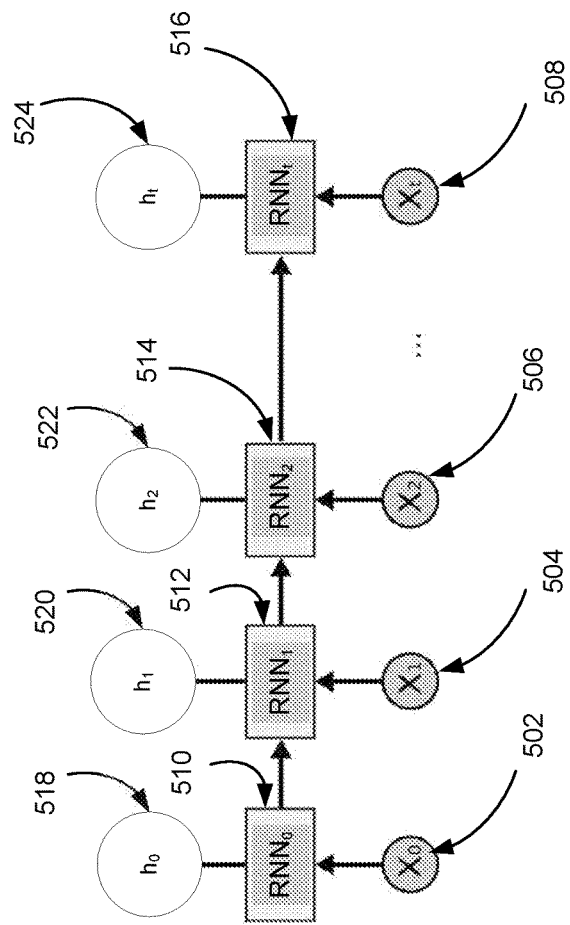
FIG. 5 illustrates an overview diagram of a recurrent neural network that can be used for encoding input peptide sequences in accordance with an embodiment.

FIG. 5 illustrates an overview diagram of a recurrent neural network that can be used for encoding input peptide sequences in accordance with an embodiment. In general, recurrent neural network (RNN) 500 uses internal states to process an input sequence $x_o$ to $x_t$ 502, 504, 506, and 508, which is an input peptide sequence (e.g., input peptide sequence 200, "ALATFTVNI" SEQ. NO. 1, represented in one-hot code) of any length for the embodiments herein. In RNN 500, connections between nodes $RNN_0$ to $RNN_t$ 510, 512, 514, and 516 form a directed graph (i.e., layers) along a sequence. Particularly, RNN 500 may include nodes that are input nodes that receive data from outside the RNN, output nodes that yield results, or hidden nodes that modify the data en route from input to output along the sequence. During the processing of an input sequence $x_o$ to $x_t$ 502, 504, 506, and 508, each node $RNN_0$ to $RNN_t$ 510, 512, 514, and 516 generates an intermediate state output, as illustrated by intermediate state outputs h0 to h2 518, 520, and 522. The final output along the sequence is final hidden state output 524.

In an embodiment, final hidden state output 524 is applied at each intermediate state output h0 to h2 518, 520, and 522 of RNN 500 to generate an attention weighted output. For example, an attention weighted output may be generated by taking a dot product of the final hidden state output and the intermediate state output for each node. In some embodiments, weights learned through the training of the neural network model may be applied to the final hidden state prior to applying the final hidden state at intermediate state outputs to generate attention weighted outputs. Further, a fixed-dimension encoding output may be generated by RNN 500 by applying final hidden state output 524 of the RNN at intermediate state outputs $h_0$ to $h_2$ 518, 520, and 522 to generate attention weighted outputs, and linearly combining the attention weighted outputs.

A fully connected layer comprising a plurality of hidden neurons, may follow an encoder, e.g., encoder 310 or 318, comprising RNN 500 to perform a classification on the attention weighted output. In an embodiment, a fully connected layer, e.g., fully connected layer 312 or 320, is configured to receive the encoded attention weighted output from an encoder, e.g., encoder 310 or 318, comprising RNN 500 and generate an output value, e.g., output 314 or 324, which represents an MHC-peptide binding affinity prediction.

As described above, a neural network model comprising RNN 500 may be trained to predict MHC-peptide binding affinity, using a plurality of batches of the training peptide sequences 1 to N 302, 304, and 306, by processing an input training peptide sequence to generate a fixed-dimension encoding output such that a final hidden state of the RNN is applied at intermediate state outputs of the RNN to generate attention weighted outputs, and the attention weighted outputs are linearly combined to generate a fixed-dimension encoding output.

Figure 6:
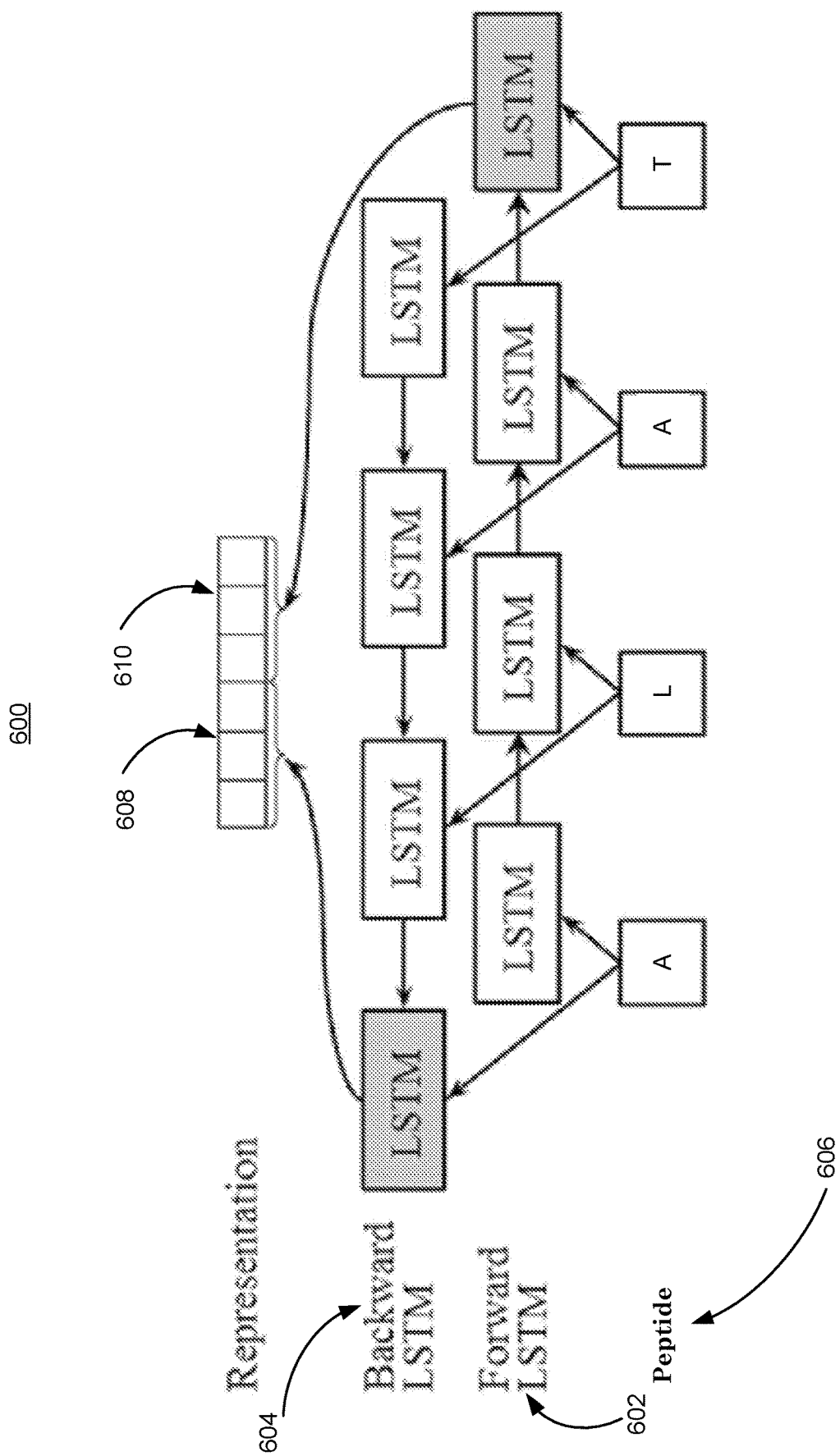
FIG. 6 illustrates an overview diagram of a bidirectional recurrent neural network that can be used for encoding input peptide sequences in accordance with an embodiment.

FIG. 6 illustrates an overview diagram of a bidirectional recurrent neural network that can be used for encoding input peptide sequences in accordance with an embodiment. In an alternative embodiment, bidirectional recurrent neural network (RNN) 600 comprising a forward RNN 602 and a backward RNN 604 may be used to process an input peptide sequence. In general, bidirectional RNNs use a finite sequence to predict or label each element of an input sequence based on the element's past and future contexts. This is done by processing an input sequence 606 of any length, such as an input peptide sequence, from left to right using forward RNN 602 and from right to left using backward RNN 604, and then concatenating the outputs 608 and 610 of the two RNNs, where the combined outputs are used to determine a fixed-dimension encoding output.

During the processing of an input peptide sequence 606, each node of forward and backward RNNs 602 and 604 generates an intermediate state output. In an embodiment, the concatenated outputs 608 and 610 represent a final hidden state output of bidirectional RNN 600 that is applied at each intermediate state output of forward and backward RNNs 602 and 604 to generate an attention weighted output. For example, the attention weighted output may be generated by taking a dot product of the final hidden state output and the intermediate state output for each node of forward and backward RNNs 602 and 604. The attention weighted outputs may then be linearly combined to generate a fixed-dimension encoding output. In some embodiments, weights learned through the training of the neural network model may be applied to the final hidden state prior to applying the final hidden state at each of the intermediate state outputs to generate attention weighted outputs.

While the recurrent neural networks illustrated in FIGS. 5 and 6 are exemplary for implementing the embodiments herein, one skilled in the art will appreciate that other recurrent neural network architectures employing, for example, Long Short-Term Memory Units (LSTMs) and/or Gated Recurrent Units (GRUs) may be utilized. As such, RNN 500 should not be construed as being strictly limited to the embodiments described herein.

Figure 7A:
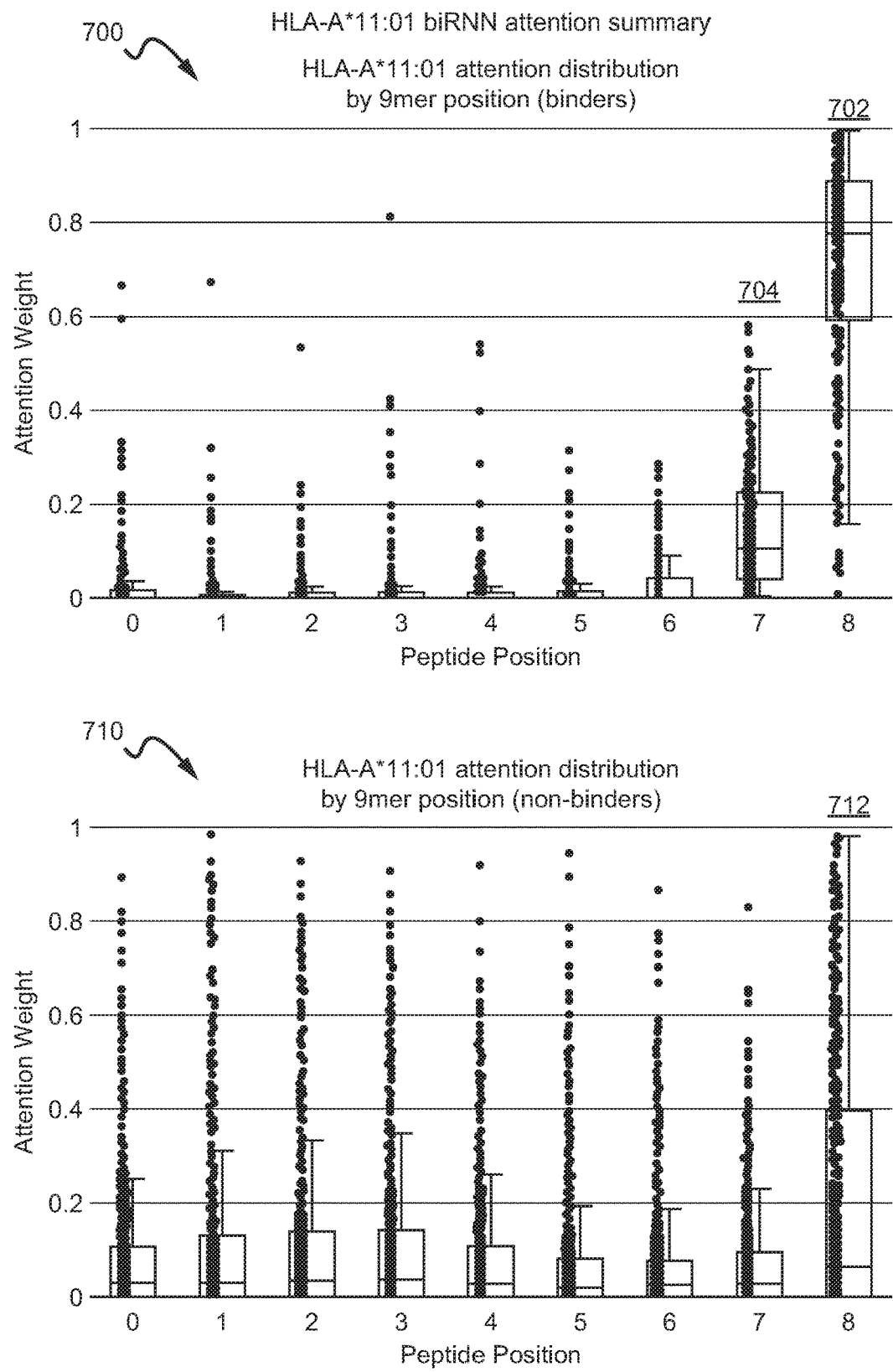
FIG. 7A illustrates a visualization of attention weights determined for peptide positions of input peptide sequences in accordance with an embodiment.

FIG. 7A illustrates a visualization of attention weights determined for peptide positions of input peptide sequences in accordance with an embodiment. Attention distributions determined using a bidirectional recurrent neural network encoder as described herein are shown for peptide positions of binding and non-binding HLA-A-1101 9-mer in plots 700 and 710, respectively. In plots 700 and 710, the RNN encoder-based models are trained on all lengths, but for visualization only, 9-mers peptides have been selected independently to average their positional attention scores. Particularly, plot 700 illustrates that the attention weight of peptide position 8 702 is the highest (having a mean distribution generally between 0.6 and 0.9) among the peptide positions for HLA-A-1101 9-mer binders, while peptide position 7 704 has the second highest mean distribution (generally between 0.05 and 0.23). Similarly, plot 710 illustrates that the attention weight of peptide position 8 712 is the highest (having a mean distribution generally between 0.0 and 0.4) among the peptide positions for HLA-A-1101 9-mer non-binders.

Figure 7C:
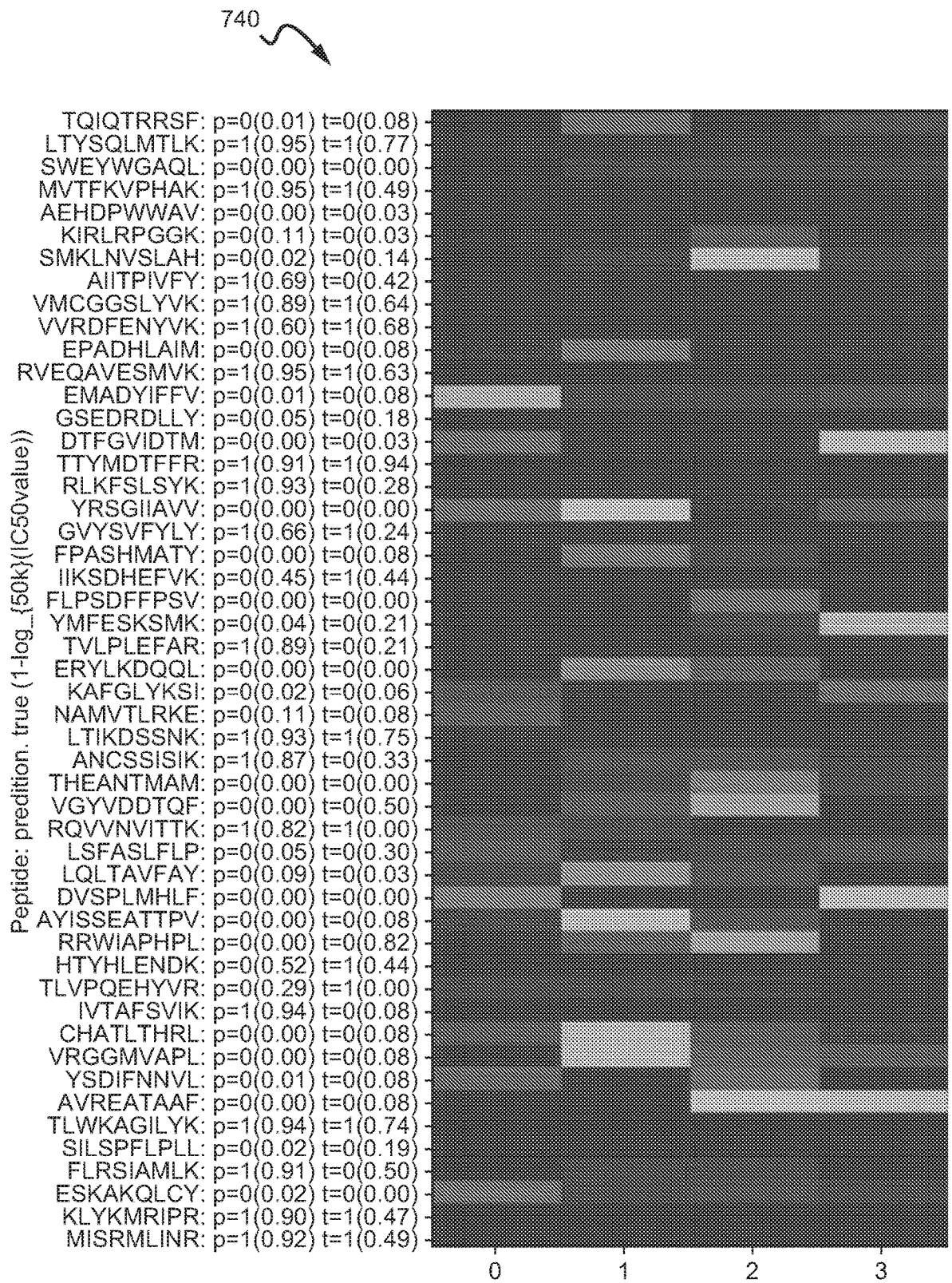
FIG. 7C illustrates a visualization of attention maps determined for peptide positions of input peptide sequences (SEQ. NOS. 4-53) in accordance with an embodiment.
Figure 7C:
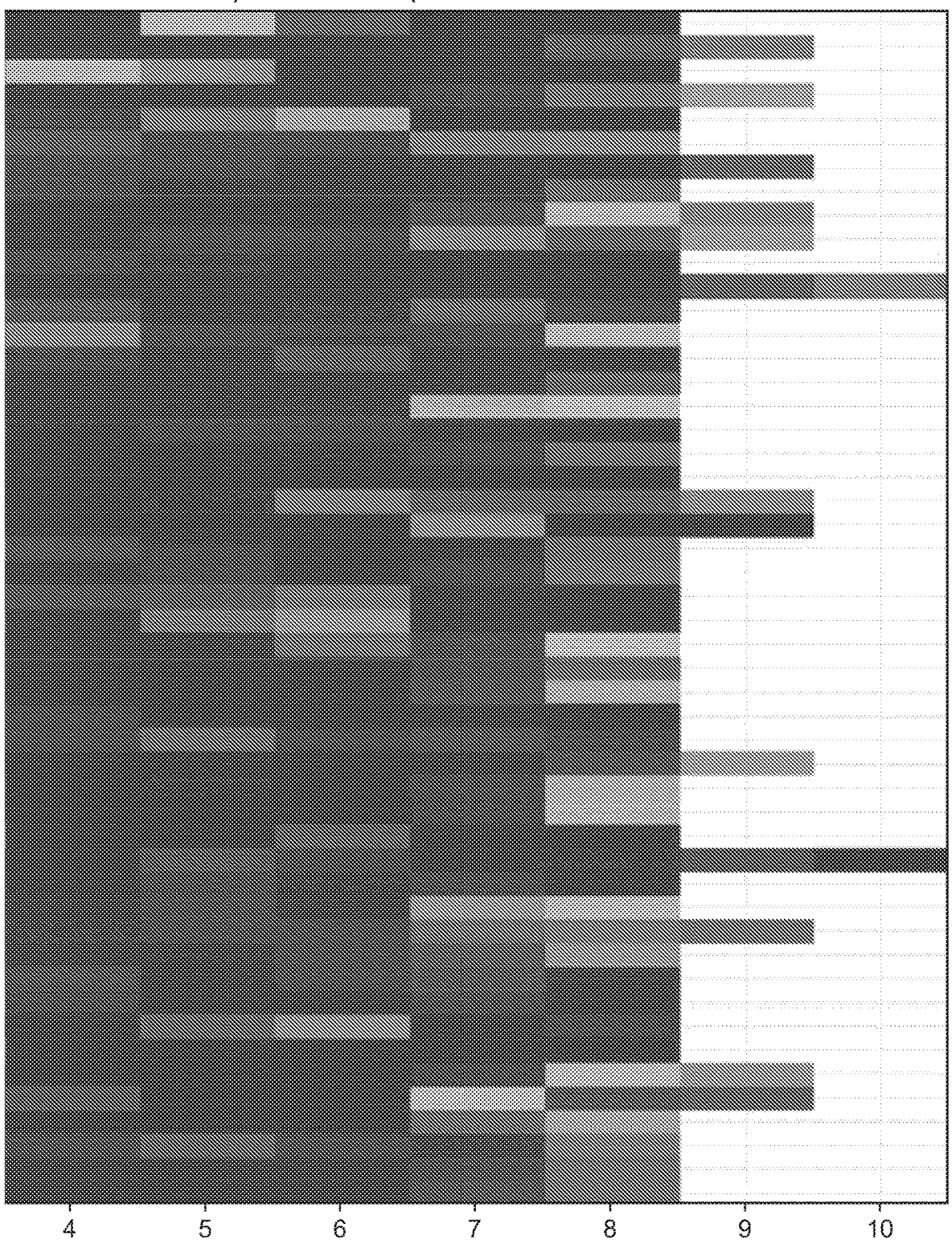

FIG. 7B illustrates a visualization of attention weights determined for peptide positions of input peptide sequences (SEQ. NOS. 2-3) in accordance with an embodiment. Plot 720 shows attention maps that illustrate attention weights for specific amino acids at different peptide positions of binding (722 and 724) and non-binding (726 and 728) HLA-A-1101 9-mer. For example, attention map 722 (and map 724 which is a filtered version of map 722) shows a relatively high attention weight for amino acid R in peptide position 8 for HLA-A-1101 9-mer binders. Similarly, attention map 726 (and map 728 which is a filtered version of map 726) shows, for example, relatively high attention weights for amino acids W, K, and R in peptide position 8 for HLA-A-1101 9-mer non-binders. Moreover, FIG. 7C illustrates a plot 740 that shows a visualization of example attention maps determined using a bidirectional recurrent neural network encoder as described herein for variable lengths of HLA-A-1101 binders (SEQ. NOS. 4-53).

Figure 8:
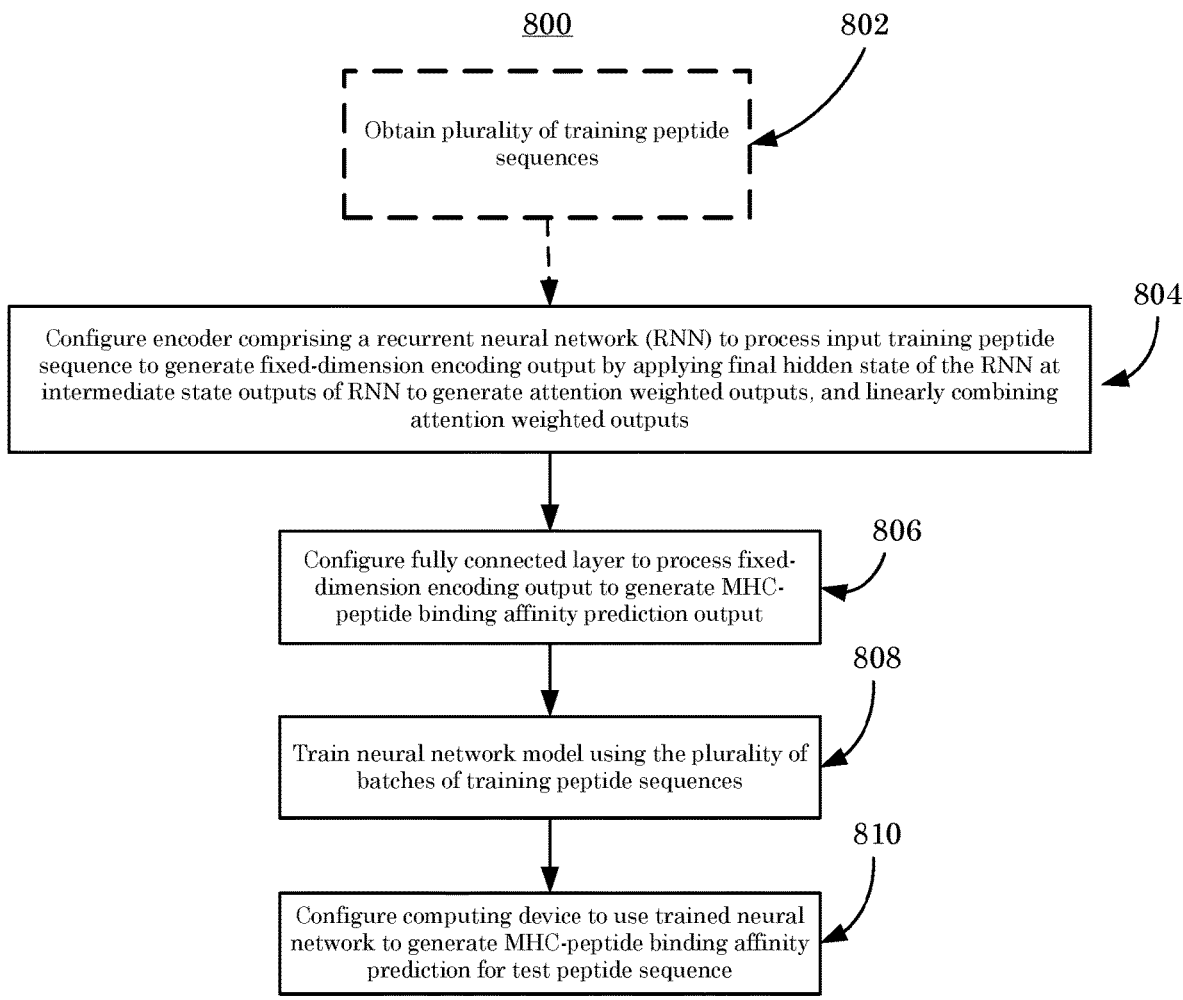
FIG. 8 illustrates a flow diagram of example operations for training a neural network model to predict MHC-peptide binding affinity using variable-length training peptide sequences in accordance with an embodiment.

FIG. 8 illustrates a flow diagram of example operations for training a neural network model to predict MHC-peptide binding affinity using variable-length training peptide sequences in accordance with an embodiment. In flow diagram 800, a plurality of training peptide sequences is obtained at step 802, e.g., by training engine 410. In an embodiment, the plurality of training peptide sequences may comprise variable sequence lengths such as, for example, sequence lengths that are between 6-20 amino acids or even 10-30 amino acids (e.g., for predicting MHC Class II-peptide binding affinity). At step 804, an encoder comprising a recurrent neural network (RNN), e.g., encoder 310, is configured to process an input training peptide sequence to generate a fixed-dimension encoding output by applying a final hidden state of the RNN at intermediate state outputs of the RNN to generate attention weighted outputs, and linearly combining the attention weighted outputs. In an embodiment, the final hidden state ($h_f$) may have other information that is desirable to consider for the attention decision appended to it. For example, in a scenario where one neural network model comprising an RNN encoder is processing an input peptide sequence and a second neural network model comprising an RNN encoder is processing an MHC allele sequence, the final hidden states of both encoders [h1_N, h2_M] may be concatenated or only the final hidden state from the other MHC allele sequence encoder may be used, such that attention weights for the peptide encoder might be decided as:

$$f([h1\_N,h2\_M],h1\_0), f([h1\_N,h2\_M],h1\_1), \ldots \\ f([h1\_N,h2\_M],h1\_N)$$

or $$f(h2\_M,h1\_0), f(h2\_M,h1\_1), \ldots f(h2\_M,h1\_N).$$

In the dual encoder scenario, it should be noted that the MHC allele sequence encoder and the peptide encoder could have similar or different architectures and could share some but not all components. For example, an amino acid embedding layer could be shared, but the sequence processing architectures could be different.

At step 806, at least one fully connected layer, e.g., fully connected layer 312, is configured to process the fixed-dimension encoding output to generate an MHC-peptide binding affinity prediction output. For example, the at least one fully connected layer may comprise a plurality of fully connected layers.

At step 808, the neural network is trained using the plurality of training peptide sequences. For example, each output value may be compared to a known labeled value, e.g., a known MHC-peptide binding affinity value corresponding to the input encoded peptide sequence, to determine a loss or error factor that can be used to determine parameter updates within the fully connected layer. For example, a stochastic gradient descent algorithm or variant thereof (such as Adagrad, RMSprop, Adam, etc.) may be used to determine the parameter updates.

At step 810, a computing device, e.g., prediction engine 420, is configured to use the trained neural network to generate an MHC-peptide binding affinity prediction for a test peptide sequence, where generating the MHC-peptide binding affinity prediction may comprise processing a test peptide sequence via the trained encoder to generate a fixed-dimension encoding output by applying a final hidden state of the RNN at intermediate state outputs of the RNN to generate attention weighted outputs, and linearly combining the attention weighted outputs. The at least one trained fully connected layer following trained encoder may then process the fixed-dimension encoding output to generate an MHC-peptide binding affinity prediction output for input test peptide sequence.

Figure 9:
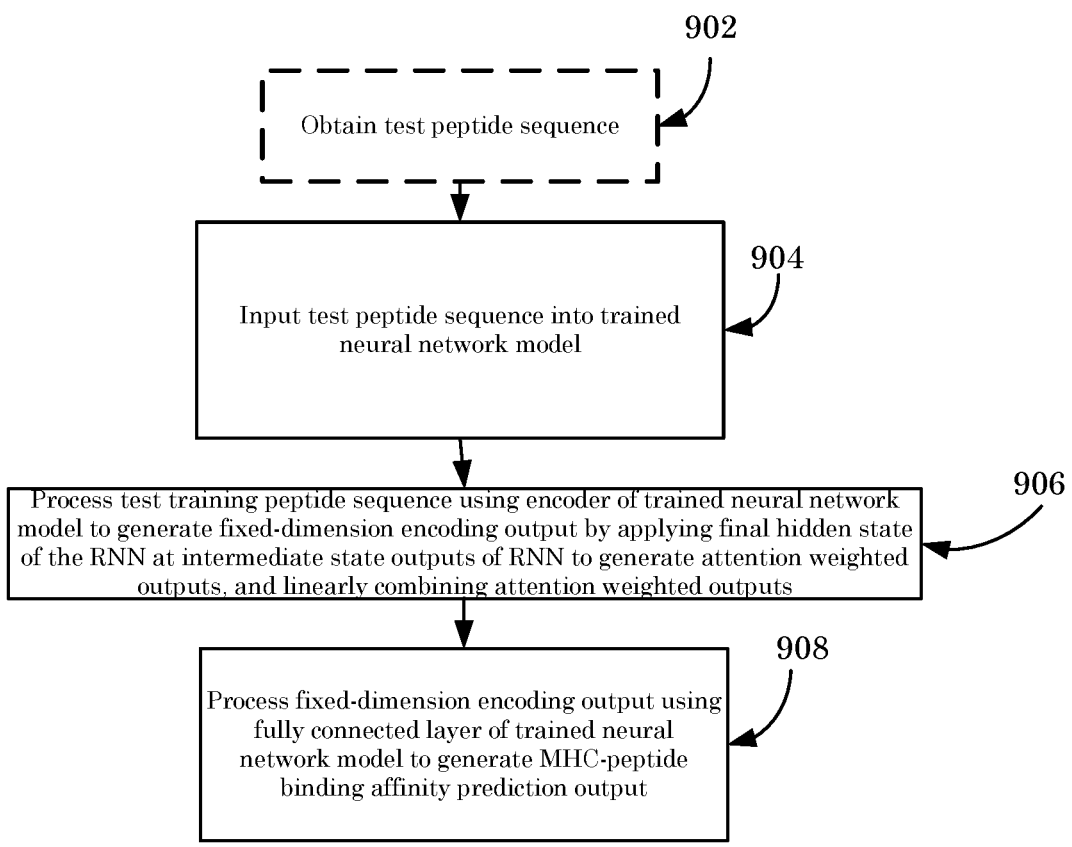
FIG. 9 illustrates a flow diagram of example operations for using a trained neural network model to predict MHC-peptide binding affinity for a test peptide sequence in accordance with an embodiment.

FIG. 9 illustrates a flow diagram of example operations for using a trained neural network model to predict MHC-peptide binding affinity for a test peptide sequence in accordance with an embodiment. In flow diagram 900, a test peptide sequence is obtained at step 902, e.g., by prediction engine 420.

At step 904, the test input sequence is input into a trained neural network model, e.g., trained neural network model 316.

At step 906, the test training peptide sequence is processed using the encoder of the trained neural network model to generate fixed-dimension encoding output by applying final hidden state of the RNN at intermediate state outputs of RNN to generate attention weighted outputs, and linearly combining attention weighted outputs.

At step 908, the fixed-dimension encoding output is processed using the fully connected layer of trained neural network model to generate an MHC-peptide binding affinity prediction output. For example, the MHC-peptide binding affinity prediction for the test peptide sequence may be associated with activating a T-cell response to a tumor.

FIG. 10 illustrates a graphical representation of neural network validation performance for variable-length peptide sequences using a neural network model in accordance with an embodiment versus alternative approaches. In chart 1000, columns A through D 1002 include 9-mer and 10-mer peptide datasets organized per allele (e.g., HLA-A-0101, 9 and HLA-A-0101, 10), and columns E and F 1004 show results for two independent neural networks per allele trained separately for 9 and 10-mer peptides without padding. For example, two neural networks trained separately using HLA-A-0101 9-mers and HLA-A-0101 10-mers without padding achieve Receiver Operating Characteristic Area Under the Curve (ROC AUC)=0.951, Precision-Recall Area Under the Curve (PR AUC)=0.812 and ROC AUC=0.766, PR AUC=0.514, respectively.

Columns G through J 1006 illustrate performance of a single neural network model trained per-allele on data from both 9-mers and 10-mers using a single-padding approach. The single-padding approach places the peptide in the center position and pads at both the start and end to a fixed length of 13. For example, when a single-padding approach is used for a model trained on both 9-mers and 10-mers of HLA-A-0101, overall performance is ROC AUC=0.933, PR AUC=0.735, and performance measured separately by peptide length is ROC AUC=0.953, PR AUC=0.810 for 9-mers, and ROC AUC=0.811, PR AUC=0.522 for 10-mers.

Columns K through N 1008 show results of a single neural network trained per-allele on data from both 9-mers and 10-mers using the expanded padding techniques. When trained on both 9-mers and 10-mers of HLA-A-0101 this model achieves overall ROC AUC=0.933, PR AUC=0.771, and when measured separately by peptide length ROC AUC=0.943, PR AUC=0.794 for 9-mers, and ROC AUC=0.865, PR AUC=0.682 for 10-mers.

Columns O through T 1010 show results of a single neural network trained per-allele on data from both 9-mers and 10-mers using a bidirectional recurrent neural network encoder and attention weighting as described herein. When trained on both 9-mers and 10-mers of HLA-A-0101 this model achieves overall ROC AUC=0.946, PR AUC=0.812, and when measured separately by peptide length ROC AUC=0.960, PR AUC=0.841 for 9-mers, and ROC AUC=0.859, PR AUC=0.699 for 10-mers. One skilled in the art will note that PR AUC is a more reliable metric to differentiate between approaches as it has been shown to be less sensitive to imbalance in the number of positive and negative examples in the data, which can lead to high ROC AUC values.

Thus, chart 1000 confirms that the technique of predicting MHC-peptide binding affinity for variable length peptide sequences using a recurrent neural network encoder and attention weighting compares favorably to results obtained from neural networks trained separately for each peptide length. Moreover, a neural network trained using the techniques described herein can provide useful and improved affinity predictions for other length peptide sequences, including those for which little or no affinity prediction data is available.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computers and interact via a network. The client-server relationship may be defined and controlled by computer programs running on the respective client and server computers.

A high-level block diagram of an exemplary client-server relationship that may be used to implement systems, apparatus and methods described herein is illustrated in FIG. 11. Client-server relationship 1100 comprises client 1110 in communication with server 1120 via network 1130 and illustrates one possible division of MHC-peptide binding affinity prediction tasks between client 1110 and server 1120. For example, client 1110 may, in accordance with the various embodiments described above, obtain a test peptide sequence; access a neural network model, e.g., via server 1120, trained using training peptide sequences; and generate an MHC-peptide binding affinity prediction using the trained neural network model. Server 1120 may, in turn, obtain a plurality of training peptide sequences; configure an encoder of a neural network model comprising a recurrent neural network (RNN) to process the input training peptide sequence to generate a fixed-dimension encoding output by applying the final hidden state of the RNN at intermediate state outputs of the RNN to generate attention weighted outputs, and linearly combining the attention weighted outputs; configure one or more fully connected layers of the neural network model to process the fixed-dimension encoding output to generate MHC-peptide binding affinity prediction output; train the neural network model using the plurality of batches of training peptide sequences; and configure a computing device to use the trained neural network model to generate an MHC-peptide binding affinity prediction for a test peptide sequence.

One skilled in the art will appreciate that the exemplary client-server relationship illustrated in FIG. 11 is only one of many client-server relationships that are possible for implementing the systems, apparatus, and methods described herein. As such, the client-server relationship illustrated in FIG. 11 should not, in any way, be construed as limiting. Examples of client devices 1110 can include cell phones, kiosks, personal data assistants, tablets, robots, vehicles, web cameras, or other types of computer devices.

Systems, apparatuses, and methods described herein may be implemented using a computer program product tangibly embodied in an information carrier, e.g., in a non-transitory machine-readable storage device, for execution by a programmable processor; and the method steps described herein, including one or more of the steps of FIGS. 8 and 9, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 12:
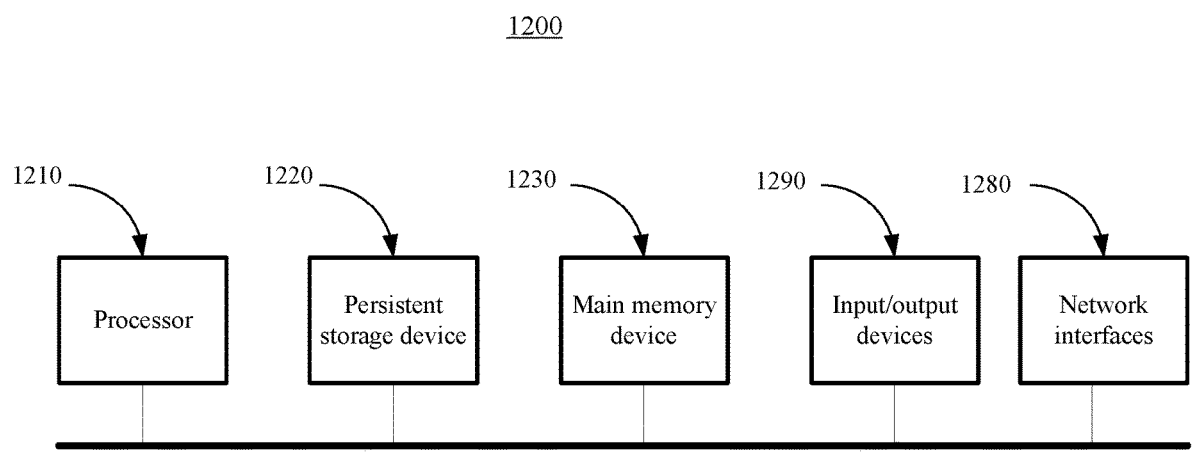
FIG. 12 illustrates a block diagram of a distributed computer system that can be used for implementing one or more aspects of the various embodiments.

A high-level block diagram of an exemplary apparatus that may be used to implement systems, apparatus and methods described herein is illustrated in FIG. 12. Apparatus 1200 comprises a processor 1210 operatively coupled to a persistent storage device 1220 and a main memory device 1230. Processor 1210 controls the overall operation of apparatus 1200 by executing computer program instructions that define such operations. The computer program instructions may be stored in persistent storage device 1220, or other computer-readable medium, and loaded into main memory device 1230 when execution of the computer program instructions is desired. For example, training engine 410 and prediction engine 420 may comprise one or more components of computer 1200. Thus, the method steps of FIGS. 8 and 9 can be defined by the computer program instructions stored in main memory device 1230 and/or persistent storage device 1220 and controlled by processor 1210 executing the computer program instructions. For example, the computer program instructions can be implemented as computer executable code programmed by one skilled in the art to perform an algorithm defined by the method steps of FIGS. 8 and 9. Accordingly, by executing the computer program instructions, the processor 1210 executes an algorithm defined by the method steps of FIGS. 8 and 9. Apparatus 1200 also includes one or more network interfaces 1280 for communicating with other devices via a network. Apparatus 1200 may also include one or more input/output devices 1290 that enable user interaction with apparatus 1200 (e.g., display, keyboard, mouse, speakers, buttons, etc.).

Processor 1210 may include both general and special purpose microprocessors and may be the sole processor or one of multiple processors of apparatus 1200. Processor 1210 may comprise one or more central processing units (CPUs), and one or more graphics processing units (GPUs), which, for example, may work separately from and/or multi-task with one or more CPUs to accelerate processing, e.g., for various deep learning and analytics applications described herein. Processor 1210, persistent storage device 1220, and/or main memory device 1230 may include, be supplemented by, or incorporated in, one or more application-specific integrated circuits (ASICs) and/or one or more field programmable gate arrays (FPGAs).

Persistent storage device 1220 and main memory device 1230 each comprise a tangible non-transitory computer readable storage medium. Persistent storage device 1220, and main memory device 1230, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1290 may include peripherals, such as a printer, scanner, display screen, etc. For example, input/output devices 1290 may include a display device such as a cathode ray tube (CRT), plasma or liquid crystal display (LCD) monitor for displaying information (e.g., a DNA accessibility prediction result) to a user, a keyboard, and a pointing device such as a mouse or a trackball by which the user can provide input to apparatus 1200.

Any or all of the systems and apparatus discussed herein, including training engine 410 and prediction engine 420 may be performed by, and/or incorporated in, an apparatus such as apparatus 1200.

One skilled in the art will recognize that an implementation of an actual computer or computer system may have other structures and may contain other components as well, and that FIG. 12 is a high-level representation of some of the components of such a computer for illustrative purposes.

The foregoing specification is to be understood as being in every respect illustrative and exemplary, but not restrictive, and the scope of the invention disclosed herein is not to be determined from the specification, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

We claim:

1. A computing system-implemented method of predicting major histocompatibility complex (MHC)-peptide binding affinity, the method comprising:
   obtaining a plurality of training peptide sequences of variable length;
   training, by one or more computing devices, a recurrent neural network (RNN) model comprising at least one fully connected layer to predict MHC-peptide binding affinity with respect to an MHC allele sequence, wherein training the RNN model comprises, for each training peptide sequence of the plurality of training peptide sequences of variable length, iteratively:
   inputting the training peptide sequence into the RNN model;
   generating a fixed-dimension encoding output by processing the training peptide sequence, wherein the processing comprises applying a final hidden state of the RNN model at intermediate states of the RNN model and attention weighting to one or more positions of the training peptide sequence;
   generating an MHC-peptide binding affinity prediction output between the training peptide sequence and the MHC allele sequence by processing the fixed-dimension encoding output using the at least one fully connected layer of the RNN model;
   determining a loss factor by comparing the attention weighting to a known MHC-peptide binding affinity value corresponding to the training peptide sequence; and
   updating at least one parameter of a set of parameters of the RNN model based on the loss factor;
   inputting a test peptide sequence into the trained RNN model; and
   generating, by the trained RNN model, an MHC-peptide binding affinity prediction output for the test peptide sequence with respect to the MHC allele sequence.

2. The method of claim 1, wherein applying the final hidden state at an intermediate state of the RNN model comprises taking a dot product, a weighted product, or other function, of the final hidden state and the intermediate state.

3. The method of claim 1, further comprising applying weights learned through the training of the RNN model to the final hidden state prior to applying the final hidden state at intermediate states of the RNN model.

4. The method of claim 1, further comprising concatenating the final hidden state with a final hidden state of an encoder of a second neural network model prior to applying the final hidden state at intermediate states of the RNN model.

5. The method of claim 4, wherein the second neural network model is configured based on the set of parameters of the trained RNN model to predict MHC-peptide binding affinity for an MHC allele input.

6. The method of claim 1, wherein the fixed-dimension encoding output generated by the RNN model comprises one or more positions each corresponding to an amino acid position of a training peptide sequence inputted into the RNN model.

7. The method of claim 6, wherein each of the one or more positions of the fixed-dimension encoding output is a single value.

8. The method of claim 1, wherein the RNN model comprises one of a Long Short Term Memory (LSTM) RNN and Gated Recurrent Unit (GRU) RNN or variant thereof.

9. The method of claim 1, wherein the RNN model comprises a bidirectional RNN model.

10. The method of claim 9, wherein the fixed-dimension encoding output is generated by concatenating outputs of the bidirectional RNN model.

11. The method of claim 1, wherein the plurality of training peptide sequences of variable length comprises two or more sequence lengths.

12. The method of claim 1, wherein the plurality of training peptide sequences is one of one-hot, BLOSUM, PAM, or learned embedding encoded.

13. The method of claim 1, wherein each training peptide sequence of the plurality of training peptide sequences is between 6-20 amino acids in length.

14. The method of claim 1, wherein each training peptide sequence of the plurality of training peptide sequences is between 10-30 amino acids in length.

15. The method of claim 1, wherein each training peptide sequence of the plurality of training peptide sequences is a positive MHC-peptide binding example.

16. The method of claim 1, wherein the test peptide sequence is between 6-20 amino acids in length.

17. The method of claim 1, wherein the test peptide sequence is between 10-30 amino acids in length.

18. The method of claim 1, wherein the test peptide sequence has a sequence length different from a sequence length of at least one of the plurality of training peptide sequences.

19. The method of claim 1, wherein the test peptide sequence is one of one-hot, BLOSUM, PAM, or learned embedding encoded.

20. The method of claim 1, wherein generating MHC-peptide binding affinity prediction output for the test peptide sequence comprises generating a single prediction value.

21. The method of claim 20, wherein the single prediction value relates to a likelihood of activating a T-cell response to a tumor.

22. The method of claim 1, wherein the at least one fully connected layer comprises two fully connected layers.

23. The method of claim 1, wherein the at least one fully connected layer comprises one of a deep convolutional neural network, a residual neural network, a densely connected convolutional neural network, a fully convolutional neural network, or an RNN.

24. The method of claim 1, wherein generating, by the trained RNN model, the MHC-peptide binding affinity prediction output for the test peptide sequence comprises:
    generating a fixed-dimension encoding output by processing the test peptide sequence, wherein the processing comprises applying a final hidden state of the RNN model at intermediate states of the RNN model and attention weighting to one or more positions of the test peptide sequence, and
    generating the MHC-peptide binding affinity prediction output by processing the fixed-dimension encoding output using the at least one fully connected layer of the trained RNN model.

25. A computer program product embedded in a non-transitory computer-readable medium comprising instructions executable by a computer processor for predicting major histocompatibility complex (MHC)-peptide binding affinity, which, when executed by a processor, cause the processor to perform one or more steps comprising:
    obtaining a plurality of training peptide sequences of variable length;
    training a recurrent neural network (RNN) model comprising at least one fully connected layer to predict MHC-peptide binding affinity with respect to an MHC allele sequence, wherein training the RNN model comprises, for each training peptide sequence of the plurality of training peptide sequences of variable length, iteratively:
        inputting the training peptide sequence into the RNN model;
        generating a fixed-dimension encoding output by processing the training peptide sequence, wherein the processing comprises applying a final hidden state of the RNN model at intermediate states of the RNN model and attention weighting to one or more positions of the training peptide sequence;
        generating an MHC-peptide binding affinity prediction output between the training peptide sequence and the MHC allele sequence by processing the fixed-dimension encoding output using the at least one fully connected layer of the RNN model;
        determining a loss factor by comparing the attention weighting to a known MHC-peptide binding affinity value corresponding to the training peptide sequence; and
        updating at least one parameter of a set of parameters of the RNN model based on the loss factor;
    inputting a test peptide sequence into the trained RNN model; and
    generating, by the trained RNN model, an MHC-peptide binding affinity prediction output for the test peptide sequence with respect to the MHC allele sequence.

26. A computing system for predicting major histocompatibility complex (MHC)-peptide binding affinity, comprising:
    a processor;
    a main memory device;
    a persistent storage device;
    a training engine executable on the processor according to software instructions stored in one of the main memory device and the persistent storage device whereby the training engine is operative to:
        train the RNN model to predict MHC-peptide binding affinity for an MHC allele sequence, wherein training the RNN model comprises, for each training peptide sequence of the plurality of training peptide sequences of variable length, operations to iteratively:
        input the training peptide sequence into the RNN model;
        generate a fixed-dimension encoding output by processing the training peptide sequence, wherein the processing comprises applying a final hidden state of the RNN model at intermediate states of the RNN model and attention weighting to one or more positions of the training peptide sequence;
        generate an MHC-peptide binding affinity prediction output between the training peptide sequence and the MHC allele sequence by processing the fixed-dimension encoding output using the at least one fully connected layer of the RNN model;
        determine a loss factor by comparing the attention weighting to a known MHC-peptide binding affinity value corresponding to the training peptide sequence; and
        update at least one parameter of a set of parameters of the RNN model based on the loss factor;
    a prediction engine in communication with the training engine whereby the prediction engine is operative to:
        obtain a test peptide sequence;
        input the test peptide sequence into the trained neural network model; and
        generate, by the trained RNN model, an MHC-peptide binding affinity prediction output for the test peptide sequence with respect to the MHC allele sequence.

27. A computing device comprising:
    a processor;
    a main memory device;
    a persistent storage device;
    a prediction engine executable on the processor according to software instructions stored in one of the main memory device and the persistent storage device whereby the prediction engine is operative to:
        obtain a test peptide sequence;
        input the test peptide sequence into a recurrent neural network (RNN) model trained to predict MHC-peptide binding affinity for an MHC allele sequence by, for each training peptide sequence of a plurality of training peptide sequences of variable length, operations to iteratively:
        input the training peptide sequence into the RNN model;
        generate a fixed-dimension encoding output by processing the training peptide sequence, wherein the processing comprises applying a final hidden state of the RNN model at intermediate states of the RNN model and attention weighting to one or more positions of the training peptide sequence;
        generate an MHC-peptide binding affinity prediction output between the training peptide sequence and the MHC allele sequence by processing the fixed-dimension encoding output using the at least one fully connected layer of the RNN model;
        determine a loss factor by comparing the attention weighting to a known MHC-peptide binding affinity value corresponding to the training peptide sequence; and
        update at least one parameter of a set of parameters of the RNN model based on the loss factor; and generate, by the trained RNN model, an MHC-peptide binding affinity prediction output for the test peptide sequence with respect to the MHC allele sequence.

\* \* \* \* \*